United States Patent
Nakajima et al.

(10) Patent No.: US 12,402,789 B2
(45) Date of Patent: Sep. 2, 2025

(54) OPHTHALMIC APPARATUS, METHOD OF CONTROLLING OPHTHALMIC APPARATUS, AND RECORDING MEDIUM

(71) Applicant: Topcon Corporation, Tokyo (JP)

(72) Inventors: Masashi Nakajima, Ageo (JP); Jun Sakai, Kuki (JP)

(73) Assignee: TOPCON CORPORATION, Tokyo (JP)

( * ) Notice: Subject to any disclaimer, the term of this patent is extended or adjusted under 35 U.S.C. 154(b) by 413 days.

(21) Appl. No.: 18/118,136

(22) Filed: Mar. 7, 2023

(65) Prior Publication Data

US 2024/0032787 A1    Feb. 1, 2024

(30) Foreign Application Priority Data

Jul. 26, 2022  (JP) .................................. 2022-118486

(51) Int. Cl.
*A61B 3/10* (2006.01)
*A61B 3/00* (2006.01)

(52) U.S. Cl.
CPC .............. *A61B 3/10* (2013.01); *A61B 3/0025* (2013.01); *A61B 3/0083* (2013.01)

(58) Field of Classification Search
CPC ....... A61B 3/10; A61B 3/0025; A61B 3/0083; A61B 3/152
USPC ....................................................... 351/206
See application file for complete search history.

(56) References Cited

U.S. PATENT DOCUMENTS

| | | | |
|---|---|---|---|
| 7,831,106 B2 | 11/2010 | Elsner et al. | |
| 8,237,835 B1 | 8/2012 | Muller | |
| 2010/0204584 A1* | 8/2010 | Ornberg | ................ G06T 7/0012 |
| | | | 600/476 |
| 2015/0085252 A1 | 3/2015 | Fujimura et al. | |
| 2016/0345822 A1 | 12/2016 | Fujimura et al. | |
| 2019/0183333 A1* | 6/2019 | Arieli | ................ A61B 3/1005 |
| 2022/0125307 A1* | 4/2022 | Nitta | ................ A61B 3/1208 |
| 2024/0041317 A1* | 2/2024 | Alasaarela | ................ A61B 3/12 |

FOREIGN PATENT DOCUMENTS

| | | |
|---|---|---|
| JP | 61-293430 A | 12/1986 |
| JP | 2010-259495 A | 11/2010 |
| JP | 2013-248376 A | 12/2013 |
| JP | 2016-185192 A | 10/2016 |

* cited by examiner

*Primary Examiner* — Mohammed A Hasan
(74) *Attorney, Agent, or Firm* — XSENSUS LLP

(57) ABSTRACT

An ophthalmic apparatus includes an optical system having an illumination and imaging optical systems, a movement mechanism, and a controller. The illumination optical system may illuminate a fundus of a subject's eye with illumination light. The movement mechanism may relatively move the subject's eye and the optical system in an optical axis direction of the imaging optical system. When a corneal curvature radius is R and a distance from a corneal apex position to an imaging aperture conjugate position substantially conjugate optically to the imaging aperture is d, the controller may control the movement mechanism so that light amount of the returning light passing through the imaging aperture becomes less than when a distance in the optical axis direction between the imaging aperture conjugate position and a position of a corneal reflection image of the illumination light is (R/2−d).

24 Claims, 21 Drawing Sheets

OPHTHALMIC APPARATUS, METHOD OF CONTROLLING OPHTHALMIC APPARATUS, AND RECORDING MEDIUM

CROSS-REFERENCE TO RELATED APPLICATION

This application is based upon and claims the benefit of priority from Japanese Patent Application No. 2022-118486, filed Jul. 26, 2022: the entire contents of which are incorporated herein by reference.

FIELD

The disclose relates to an ophthalmic apparatus, method of controlling the ophthalmic apparatus, and a recording medium.

BACKGROUND

Fundus cameras that photograph a fundus of a subject's eye are configured to acquire fundus images by receiving returning light from the fundus illuminated with illumination light. It is known that flare occurs in the fundus images acquired by such fundus cameras due to the corneal reflection light from the cornea, which has a higher reflectance than the fundus, guided to the imaging optical system (e.g., Japanese Unexamined Patent Application Publication No. 2016-185192).

For example, Japanese Unexamined Patent Application Publication No. 2016-185192 discloses a method of changing the amount of displacement of the alignment target position in accordance with the size information of the pupil region.

SUMMARY

One aspect of embodiments is an ophthalmic apparatus, including: an optical system including an illumination optical system and an imaging optical system, the illumination optical system being configured to illuminate a fundus of a subject's eye with illumination light, the imaging optical system having an imaging aperture and being configured to guide returning light from the subject's eye having passed through the imaging aperture to an imaging sensor; a movement mechanism configured to relatively move the subject's eye and the optical system in an optical axis direction of the imaging optical system; and a controller configured to control the movement mechanism, wherein when a corneal curvature radius is R and a distance from a corneal apex position to an imaging aperture conjugate position substantially conjugate optically to the imaging aperture is d, the controller is configured to control the movement mechanism so that light amount of the returning light passing through the imaging aperture becomes less than when a distance in the optical axis direction between the imaging aperture conjugate position and a position of a corneal reflection image of the illumination light is (R/2−d).

Another aspect of the embodiments is an ophthalmic apparatus, including: an illumination optical system configured to illuminate a fundus of a subject's eye with illumination light; an imaging optical system having an imaging aperture and configured to guide returning light from the subject's eye having passed through the imaging aperture to an imaging sensor; an imaging aperture movement mechanism configured to move the imaging aperture in an optical axis direction of the imaging optical system; and a controller configured to control the imaging aperture movement mechanism to change a distance in the optical axis direction of the imaging optical system between an imaging aperture conjugate position substantially conjugate optically to the imaging aperture and a position of a corneal reflection image of the illumination light.

Still another aspect of the embodiments is a method of controlling an ophthalmic apparatus including: an optical system including an illumination optical system and an imaging optical system, the illumination optical system being configured to illuminate a fundus of a subject's eye with illumination light, the imaging optical system having an imaging aperture and being configured to guide returning light from the subject's eye having passed through the imaging aperture to an imaging sensor, a movement mechanism configured to relatively move the subject's eye and the optical system in an optical axis direction of the imaging optical system; and a controller configured to control the movement mechanism. The method of controlling the ophthalmic apparatus includes a control step of controlling the movement mechanism so that light amount of the returning light passing through the imaging aperture becomes less than when a distance in the optical axis direction between an imaging aperture conjugate position substantially conjugate optically to the imaging aperture and a position of a corneal reflection image of the illumination light is (R/2−d), when a corneal curvature radius is R and a distance from a corneal apex position to the imaging aperture conjugate position is d.

Still another aspect of the embodiments is a method of controlling an ophthalmic apparatus including: an illumination optical system configured to illuminate a fundus of a subject's eye with illumination light, an imaging optical system having an imaging aperture and configured to guide returning light from the subject's eye having passed through the imaging aperture to an imaging sensor; an imaging aperture movement mechanism configured to move the imaging aperture in an optical axis direction of the imaging optical system; and a controller configured to control the imaging aperture movement mechanism to change a distance in the optical axis direction of the imaging optical system between a position substantially conjugate optically to the imaging aperture and a position of a corneal reflection image of the illumination light. The method of controlling the ophthalmic apparatus includes a control step of controlling the imaging aperture movement mechanism so that light amount of the returning light passing through the imaging aperture becomes less than when a distance in the optical axis direction between an imaging aperture conjugate position substantially conjugate optically to the imaging aperture and a position of a corneal reflection image of the illumination light is (R/2−d), when a corneal curvature radius is R and a distance from a corneal apex position to the imaging aperture conjugate position is d.

Still another aspect of the embodiments is a computer readable non-transitory recording medium in which a program for causing a computer to execute each step of the method of controlling the ophthalmic apparatus described above is recorded.

DETAILED DESCRIPTION

Figure 1:
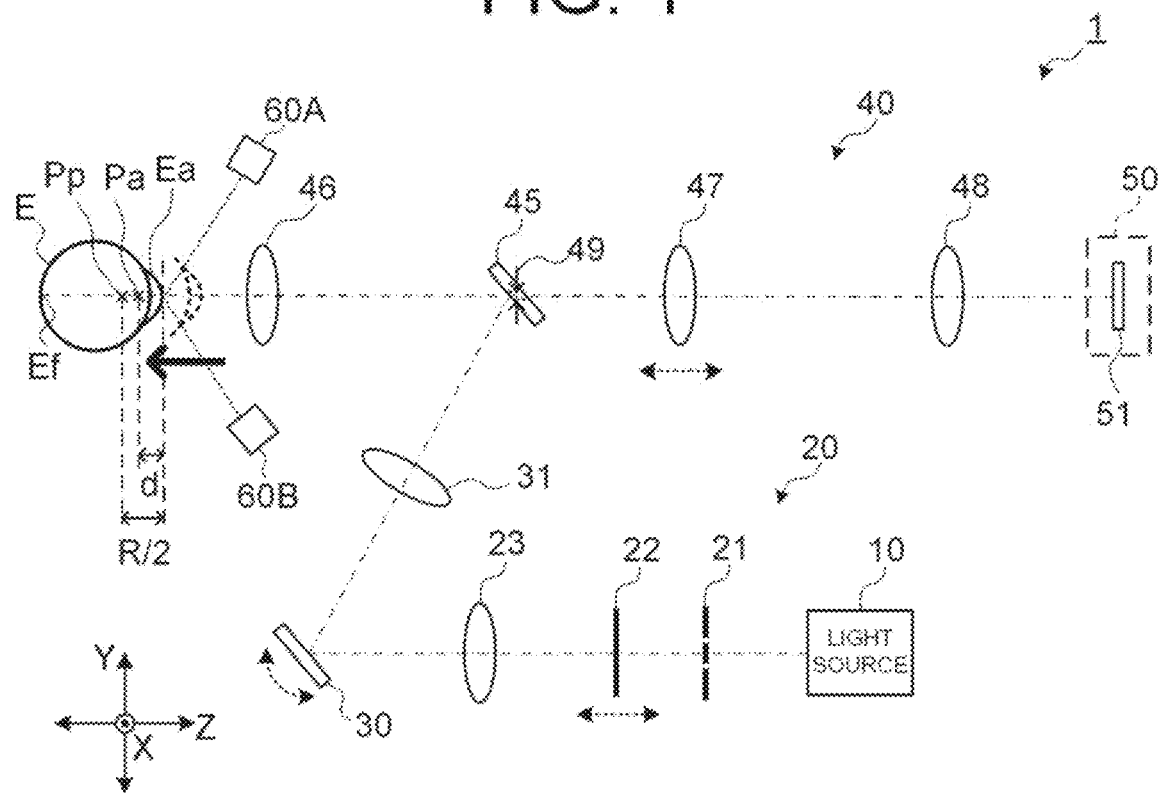
FIG. 1 is a schematic diagram illustrating an example of a configuration of an optical system of an ophthalmic apparatus according to a first embodiment.

With the method disclosed in Japanese Unexamined Patent Application Publication No. 2016-185192, it is difficult to suppress the occurrence of flare with high precision in the pupil region alone, and depending on the subject's eye, it may not be possible to sufficiently suppress the occurrence of flare included in the fundus images, or even when the occurrence of flare can be suppressed, it may result in degradation of the fundus image quality.

According to some embodiments of the present invention, a new technique for suppressing the occurrence of flare with high precision using a simple configuration while suppressing degradation of image quality can be provided.

Referring now to the drawings, exemplary embodiments of an ophthalmic apparatus, a method of controlling the ophthalmic apparatus, a program, and a recording medium according to the present invention are described below. The contents of the document cited in the present specification can be appropriately incorporated as contents of the following embodiments.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An ophthalmic apparatus according to some embodiments is provided with an optical system including an illumination optical system and an imaging (photography) optical system. The illumination optical system is configured to illuminate a fundus of a subject's eye with illumination light. The imaging optical system has an imaging (photographic) aperture and is configured to guide returning light from the subject's eye having passed through the imaging aperture to an imaging sensor. Here, a corneal curvature radius is R and a distance from the a corneal apex position to an imaging aperture conjugate position substantially conjugate optically to the imaging aperture (hereinafter sometimes referred to as the gap length) is d. In this case, the ophthalmic apparatus is configured to change a relative position of the optical system on an optical axis direction of the imaging optical system or to move the imaging aperture in the optical axis direction described above so that light amount of the returning light passing through the imaging aperture becomes less than when a distance in the optical axis direction between the imaging aperture conjugate position and a position of a corneal reflection image of the illumination light is (R/2−d).

In some embodiments, the corneal curvature radius described above is a parameter in a known schematic eye or a corneal curvature radius of the subject's eye. The imaging aperture conjugate position is a position substantially conjugate optically to the imaging aperture on the optical axis of the imaging optical system and near the corneal apex of the subject's eye. In some embodiments, the corneal reflection image is a Purkinje image.

This allows to adjust the relative position of the optical system to the subject's eye with high precision without unnecessarily moving the optical system, or to move the imaging aperture with high precision without moving the optical system. As a result, the occurrence of flare included in the fundus images can be suppressed with high precision using a simple configuration, while suppressing the degradation of fundus image quality.

It should be noted that the ophthalmic apparatus according to embodiments may be an apparatus that can acquire images of a site other than the fundus of the subject's eye. Even in this case, the occurrence of flare included in the images of a desired site of the subject's eye can be suppressed with high precision using a simple configuration, while suppressing the degradation of image quality of the images.

A method of controlling the ophthalmic apparatus according to the embodiments includes one or more steps for realizing the processing executed by a processor (computer) in the ophthalmic apparatus according to the embodiments. A program according to the embodiments causes the processor to execute each step of the method of controlling the ophthalmic apparatus according to the embodiments. A recording medium (storage medium) according to the embodiments is a computer readable non-transitory recording medium (storage medium) on which the program according to the embodiments is recorded.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

Hereinafter, the case will be described in which the ophthalmic apparatus according to the embodiments photographs the fundus using a slit scan method. However, the configuration of the ophthalmic apparatus according to the embodiments is not limited thereto.

First Embodiment

<Ophthalmic Apparatus>

An ophthalmic apparatus according to a first embodiment is configured to illuminate a fundus of a subject's eye while moving an irradiated position (irradiated range) of slit-shaped illumination light, and to receive returning light from the fundus using an image sensor with a one-dimensional or two-dimensional array of light receiving elements. Light receiving result of the returning light is read out from the light receiving element(s) at light receiving position of the returning light corresponding to the irradiated position of the illumination light, in synchronization with the movement timing of the irradiated position of the illumination light.

[Configuration of Optical System]

FIG. 1 illustrates an example of a configuration of an optical system of the ophthalmic apparatus according to the first embodiment. In FIG. 1, for convenience of explanation, a left/right direction (i.e., horizontal direction) orthogonal to an optical axis of the optical system (imaging optical system) is regarded as the X direction, a up/down direction (i.e., vertical direction) orthogonal to the optical axis of the optical system is regarded as the Y direction, and the optical axis direction (i.e., front/back direction, working distance direction) of the optical system is regarded as the Z direction.

The ophthalmic apparatus 1 according to the first embodiment includes a light source 10, an illumination optical system 20, an optical scanner 30, an imaging optical system 40, and an imaging device 50. In some embodiments, the illumination optical system 20 includes at least one of the light source 10 or the optical scanner 30 (or the optical scanner 30 and a relay lens 31 described below). In some embodiments, the imaging optical system 40 includes the imaging device 50. Hereinafter, it is assumed that the illumination optical system 20 includes the light source 10.

(Light Source 10)

The light source 10 includes a visible light source that generates light in the visible region. For example, the light source 10 generates light having a central wavelength in the wavelength range of 420 nm to 700 nm. This type of light source 10 includes, for example, an LED (Light Emitting Diode), an LD (Laser Diode), a halogen lamp, or a xenon lamp. In some embodiments, the light source 10 includes an infrared light source (near-infrared light source) that generates light in the infrared region (near-infrared region). In some embodiments, the light source 10 includes a white light source or a light source capable of outputting light with each color component of RGB. In some embodiments, the light source 10 includes a light source capable of switching to output the light in infrared region or the light in visible region. The light source 10 is arranged at a position non-conjugate optically to the fundus Ef and the iris, respectively.

(Illumination Optical System 20)

The illumination optical system 20 generates slit-shaped illumination light using the light from the light source 10. The illumination optical system 20 guides the generated illumination light to the optical scanner 30.

The illumination optical system 20 includes an iris aperture 21, a slit (slit aperture diaphragm) 22, and a relay lens 23. The light from the light source 10 passes through the aperture(s) formed in the iris aperture 21, passes through the aperture formed in the slit 22, and is transmitted through the relay lens 23. The relay lens 23 includes one or more lenses. The light transmitted through the relay lens 23 is guided to the optical scanner 30.

(Iris Aperture 21)

The iris aperture 21 (specifically, aperture(s) described below) can be arranged at a position substantially conjugate optically to the iris (pupil) of a subject's eye E. In the iris aperture 21, one or more apertures are formed at position(s) away from an optical axis of the illumination optical system 20. For example, two apertures having a predetermined thickness along a circumferential direction centered with the optical axis are formed in the iris aperture 21. The aperture formed in the iris aperture 21 defines an incident position (incident shape) of the illumination light on the iris of the subject's eye E. For example, by forming the two apertures at the positions away from the optical axis of the illumination optical system 20, when the pupil center of the subject's eye E is arranged on the optical axis of the illumination optical system 20, the illumination light can enter into the eye from positions deviated from the pupil center (specifically, point-symmetrical positions centered on the pupil center), In some embodiments, an optical element for deflecting the light from the light source 10 is positioned so that the light amount distribution in a direction connecting the aperture formed in the iris aperture 21 and an aperture formed in the slit 22 is maximized.

Further, the light amount distribution of the light passing through the aperture(s) formed in the iris aperture 21 can be changed by changing a relative position between the light source 10 and the aperture(s) formed in the iris aperture 21.

(Slit 22)

The slit 22 (specifically, aperture(s) described below) can be arranged at a position substantially conjugate optically to the fundus Ef of the subject's eye E. For example, in the slit 22, the aperture is formed extending in a direction corresponding to a line direction (row direction) that is read out from the image sensor 51 described below using the rolling shutter method. The aperture formed in the slit 22 defines an irradiated pattern of the illumination light on the fundus Ef of the subject's eye E. The direction in which the aperture formed in the slit 22 extends may be described as a slit direction.

The slit 22 can be moved in the optical axis direction of the illumination optical system 20 using a movement mechanism (movement mechanism 22D described below). The movement mechanism moves the slit 22 in the optical axis direction, under the control from the controller 100 described below. For example, the controller 100 described below controls the movement mechanism in accordance with the state of the subject's eye E. This allows to move the position of the slit 22 in accordance with a state of the subject's eye E (specifically, the dioptric power (diopter scale) or the shape of the fundus Ef).

The light from the light source 10 that has passed through the aperture(s) formed in the iris aperture 21 is output as the slit-shaped illumination light by passing through the aperture formed in the slit 22. The slit-shaped illumination light is transmitted through the relay lens 23, and is guided to the optical scanner 30. For example, the slit 22 generates the slit-shaped illumination light parallel to the X direction at the fundus Ef (or fundus conjugate position) in the focused state. In this case, the optical scanner 30 deflects the generated slit-shaped illumination light in the Y direction at the fundus Ef (or fundus conjugate position) in the focused state.

(Optical Scanner 30)

The optical scanner 30 is placed at a position substantially conjugate optically to the iris of the subject's eye E. The optical scanner 30 deflects the slit-shaped illumination light transmitted through the relay lens 23 (slit-shaped light passing through the aperture formed in the slit 22). Specifically, the optical scanner 30 deflects the slit-shaped illumination light for sequentially illuminating a predetermined illumination range of the fundus Ef to guide the illumination light to a perforated mirror 45 described below, while changing the deflection angle within a predetermined deflection angle range with the iris or the vicinity of the iris of the subject's eye E as a scan center position. The optical scanner 30 can deflect the illumination light one-dimensionally or two-dimensionally.

In case that the optical scanner 30 deflects the illumination light one-dimensionally, the optical scanner 30 includes a galvano scanner that deflects the illumination light within a predetermined deflection angle range with reference to a predetermined deflection direction. The galvano scanner deflects the illumination light so that the slit-shaped illumination light irradiated on the fundus Ef moves in a direction that intersects the slit direction.

In case that the optical scanner 30 deflects the illumination light two-dimensionally, the optical scanner 30 includes a first galvano scanner and a second galvano scanner. The first galvano scanner deflects the illumination light so as to move the irradiated position of the illumination light in a horizontal direction orthogonal to the optical axis of the illumination optical system 20. The second galvano scanner deflects light deflected by the first galvano scanner so as to move the irradiated position of the illumination light in a vertical direction orthogonal to the optical axis of the illumination optical system 20.

Examples of scan mode for moving the irradiated position of the illumination light using the optical scanner 30 include a horizontal scan, a vertical scan, a cross scan, a radial scan, a circle scan, a concentric scan, and a helical (spiral) scan.

A relay lens 31 is arranged between the optical scanner 30 and the perforated mirror 45. The relay lens 31 includes one or more lenses.

In some embodiments, at least one of a black dot or a focus indicator optical system is placed between the optical scanner 30 and the perforated mirror 45.

The black dot is arranged at a position substantially conjugate optically to a position of a center ghost formed by reflection of the illumination light on the lens surface of the objective lens 46 described below.

The focus indicator optical system projects focus indicator(s) onto the fundus Ef of the subject's eye E, when focus control is performed. Light (focus indicator light) output from the focus indicator optical system is projected onto the fundus Ef of the subject's eye E. Fundus reflection light of the focus indicator light passes through the hole formed in the perforated mirror 45, and is detected by the image sensor 51 in the imaging device 50. Light receiving image (split indicators) captured by the image sensor 51 is displayed on a display means not shown in the figure. For example, the controller 100 described below analyzes the position(s) of the split indicator(s) according to the Scheiner principle, and moves each of the focusing lens 47 and the focus indicator optical system, which are described below, in the optical axis direction to perform focusing (automatic focus function). Alternatively, the user may perform focusing manually while visually checking the split indicators.

(Imaging Optical System 40)

The imaging optical system 40 guides the illumination light deflected by the optical scanner 30 to the fundus Ef of the subject's eye E, and also guides the returning light of the illumination light from the fundus Ef to the imaging device 50.

In the imaging optical system 40, an optical path of the illumination light from the optical scanner 30 and an optical path of the returning light of the illumination light from the fundus Ef are coupled. By using the perforated mirror 45 as an optical path coupling member to couple these optical paths, it enables pupil division between the illumination light and the returning light of the illumination light.

The imaging optical system 40 includes the perforated mirror 45, the objective lens 46, the focusing lens 47, a lens 48, and an imaging aperture 49. The lens 48 includes one or more lenses.

(Perforated Mirror 45)

In the perforated mirror 45, the hole is formed. The hole is arranged on the optical axis of the imaging optical system 40. The hole of the perforated mirror 45 is arranged at a position substantially conjugate optically to the iris of the subject's eye E. The perforated mirror 45 reflects the illumination light from the optical scanner 30 (relay lens 31) toward the objective lens 46, on the peripheral region of the hole.

That is, the perforated mirror 45 is configured to couple the optical path of the illumination optical system 20 (optical path from the optical scanner 30) and the optical path of the imaging optical system 40 arranged in an optical axis direction passing through the hole, and also to guide the illumination light reflected on the peripheral region of the hole to the fundus Ef.

(Focusing Lens 47)

The focusing lens 47 can be moved in an optical axis direction of the imaging optical system 40 using a movement mechanism (not shown). The movement mechanism moves the focusing lens 47 in the optical axis direction under the control from the controller 100 described below. This allows to image the returning light of the illumination light passing through the hole of the perforated mirror 45 on the light receiving surface of the image sensor 51 in the imaging device 50 in accordance with the state of the subject's eye E.

In the imaging optical system 40 with this configuration, the illumination light (or focus indicator light) from the optical scanner 30 is reflected toward the objective lens 46 on the peripheral region of the hole formed in the perforated mirror 45. The illumination light reflected on the peripheral region of the perforated mirror 45 is refracted by the objective lens 46, enters into the eye through the pupil of the subject's eye E, and illuminates the fundus Ef of the subject's eye E. In addition, for example, the focus indicator light reflected on the peripheral region of the perforated mirror 45 is refracted by the objective lens 46, enters into the eye through the pupil of the subject's eye E, and is projected onto the fundus Ef of the subject's eye E.

The returning light of the illumination light from the fundus Ef (or fundus reflection light of the focus indicator light) is refracted by the objective lens 46, passes through the hole of the perforated mirror 45, is transmitted through the focusing lens 47, and is imaged on the light receiving surface of the image sensor 51 in the imaging device 50 through the lens 48.

(Imaging Aperture 49)

The imaging aperture 49 can be arranged at a position substantially conjugate optically to the iris (pupil) of the subject's eye E, and limits the light amount of the returning light of the illumination light from the subject's eye E guided to the image sensor 51. In the imaging aperture 49, an aperture, which passes through the optical axis of the imaging optical system 40, is formed.

The imaging aperture 49 is placed between the perforated mirror 45 and the focusing lens 47. In some embodiments, the imaging aperture 49 is provided in the hole formed in the perforated mirror 45.

(Imaging Device 50)

The imaging device 50 includes the image sensor 51 receiving the returning light of the illumination light that has been guided from the fundus Ef of the subject's eye E through the imaging optical system 40. The imaging device 50 can perform readout control of the light receiving result of the returning light under the control from the controller 100 described below.

(Image Sensor 51)

The image sensor 51 realizes the function as a pixelated photodetector. The light receiving surface (detecting surface, imaging surface) of the image sensor 51 can be arranged at a position substantially conjugate optically to the fundus Ef.

The light receiving result(s) obtained using the image sensor 51 is/are read out using a rolling shutter method under the control from the controller 100 described below.

The image sensor 51 with this configuration includes the CMOS image sensor. In this case, the image sensor 51 includes a plurality of pixels (light receiving elements). The plurality of pixels includes a plurality of pixel groups arranged in a column direction. Each of the plurality of pixel groups includes pixels arranged in a row direction. Specifically, the image sensor 51 includes a plurality of pixels arranged two-dimensionally, a plurality of vertical signal lines, and a horizontal signal line. Each pixel includes a photodiode (light receiving element), and a capacitor. The vertical signal lines are provided for each pixel group in the column direction (vertical direction) orthogonal to the row direction (horizontal direction). Each of the vertical signal lines is selectively electrically connected to the pixel group in which the electrical charge corresponding to the light receiving result is accumulated. The horizontal signal line is selectively electrically connected to the vertical signal lines. Each of the pixels accumulates the electrical charge corresponding to the light receiving result of the returning light. The accumulated electrical charge is read out sequentially for each pixel group in the row direction, for example. For example, for each line in the row direction, a voltage corresponding to the electrical charge accumulated in each pixel is supplied to the vertical signal line. The vertical signal lines are selectively electrically connected to the horizontal signal line. By performing readout operation for each line in the row direction described above sequentially in the vertical direction, the light receiving results of the plurality of pixels arranged two-dimensionally can be read out.

By capturing (reading out) the light receiving results of the returning light using the rolling shutter method for this type of image sensor 51, the light receiving image corresponding to the desired virtual opening shape extending in the row direction is acquired. Such control is disclosed in, for example, U.S. Pat. Nos. 7,831,106, 8,237,835, and the like.

Figure 2:
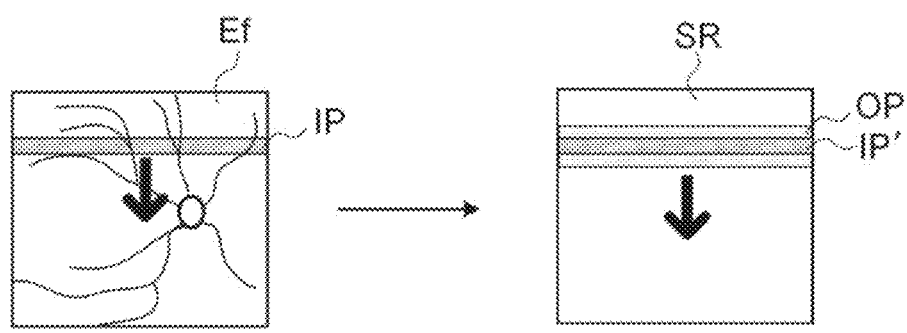
FIG. 2 is a schematic diagram for explaining an operation of the ophthalmic apparatus according to the first embodiment.

FIG. 2 shows a diagram describing the operation of the ophthalmic apparatus 1 according to the first embodiment. FIG. 2 schematically represents an irradiated range IP of the slit-shaped illumination light irradiated on the fundus Ef and a virtual opening range OP on the light receiving surface SR of the image sensor 51.

For example, the controller 100 described below deflects the slit-shaped illumination light formed by the illumination optical system 20, using the optical scanner 30. Thereby, the irradiated range IP of the slit-shaped illumination light is sequentially moved in a direction (for example, the vertical direction) orthogonal to the slit direction (for example, the row direction, the horizontal direction) on the fundus Ef.

On the light receiving surface SR of the image sensor 51, by changing the pixels to be read out in units of lines by the controller 100 described below, the virtual opening range OP is set. The opening range OP is preferable to be the light receiving range IP' of the returning light of the illumination light on the light receiving surface SR or wider than the light receiving range IP'. The controller 100 described below performs the movement control of the opening range OP in synchronization with the movement control of the irradiated range IP of the illumination light. Thereby, without being affected by unnecessary scattered light, high quality images of the fundus Ef with strong contrast can be acquired using a simple configuration.

In some embodiments, the image sensor 51 is configured using one or more line sensors.

In some embodiments, the imaging optical system 40 described below includes an optical element such as a correction lens that can be inserted into and removed from an optical path of the returning light in accordance with the wavelength range (central wavelength) of the light emitted from the light source 10, in order to image the returning light from the subject's eye on an imaging surface of the image sensor 51 in the imaging device 50 in the focused state regardless of the wavelength range (center wavelength) of the returning light from the subject's eye E.

Furthermore, the ophthalmic apparatus 1 can be provided with two or more anterior segment cameras that can be used to perform position matching of the optical system (illumination optical system 20 and imaging optical system 40) with respect to the subject's eye E. In some embodiments, one of the two or more anterior segment cameras is the image sensor 51. In the first embodiment, the ophthalmic apparatus 1 includes anterior segment cameras 60A and 60B.

(Anterior segment cameras 60A and 60B)

The anterior segment cameras 60A and 60B are used for obtaining relative position between the optical system of the ophthalmic apparatus 1 and the subject's eye E in the same manner as the method disclosed in Japanese Unexamined Patent Application Publication No. 2013-248376, for example. The anterior segment cameras 60A and 60B are provided on a surface of the subject's eye side of a body, in which the optical system is housed, of the ophthalmic apparatus 1. The anterior segment cameras 60A and 60B are provided at positions away from the optical axis of the imaging optical system 40, and photographs an anterior segment Ea of the subject's eye E from different directions. The ophthalmic apparatus 1 obtains a three-dimensional relative position between the optical system and the subject's eye E, by analyzing two anterior segment images acquired substantially simultaneously from different directions by the anterior segment cameras 60A and 60B. The analysis of the two anterior segment images may be the same as the analysis disclosed in Japanese Unexamined Patent Application Publication No. 2013-248376.

In the present examples, the position of the subject's eye E (that is, the relative position between the subject's eye E and the optical system) is obtained using two or more anterior segment cameras. However, a method of obtaining the position of the subject's eye E is not limited to this. For example, the position of the subject's eye E can be obtained by analyzing the front image (for example, the observation image of the anterior segment Ea) of the subject's eye E. Alternatively, means for projecting an indicator onto a cornea of the subject's eye E can be provided. Thereby, the position of the subject's eye E can be obtained based on the projected position of this indicator (that is, the detection state of the corneal reflection light flux of this indicator).

[Configuration of Control System]

Figure 3:
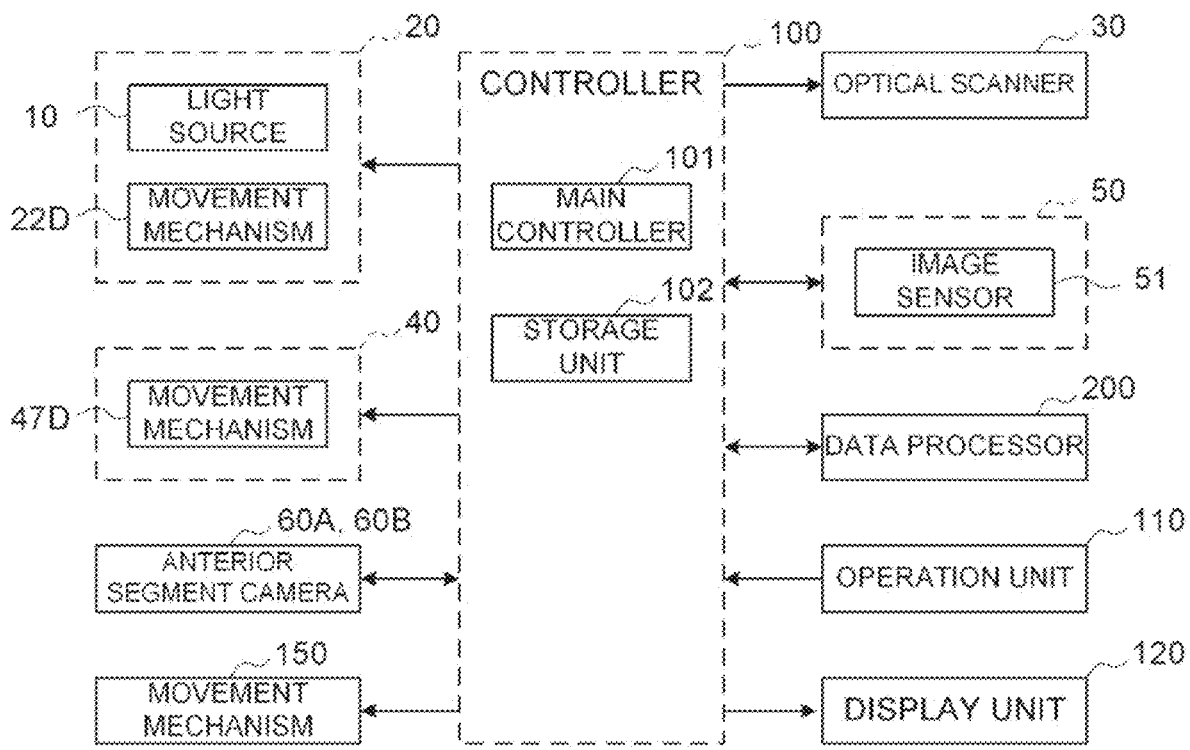
FIG. 3 is a functional block diagram illustrating an example of a configuration of a control system of the ophthalmic apparatus according to the first embodiment.

FIG. 3 shows a block diagram of an example of a configuration of a control system of the ophthalmic apparatus 1 according to the first embodiment. In FIG. 3, like reference numerals designate like parts as in FIG. 1, and the redundant explanation may be omitted as appropriate.

The control system (processing system) of the ophthalmic apparatus 1 is configured with the controller 100 as a center. It should be noted that at least a part of the configuration of the control system may be included in the ophthalmic apparatus 1.

(Controller 100)

The controller 100 controls each part of the ophthalmic apparatus 1. The controller 100 includes a main controller 101 and a storage unit 102. The main controller 101 includes a processor and executes the control processing of each part of the ophthalmic apparatus 1 by executing processing according to the program(s) stored in the storage unit 102.

(Main Controller 101)

The main controller 101 performs control for the illumination optical system 20 including the light source 10, control for the optical scanner 30, control for the imaging optical system 40, control for the imaging device 50, control for the anterior segment cameras 60A and 60B, control for the movement mechanism 150, and control for the data processor 200.

Examples of the control for the illumination optical system 20 include control for the light source 10 and control for the movement mechanism 22D.

Examples of the control for the light source 10 include switching the light source on and off (or switching the wavelength region of the light), and changing the light amount of the light source. In the case that the light source 10 can change the central wavelength of the emitted light, examples of the control for the light source 10 further include change control of the central wavelength of the emitted light.

In some embodiments, the main controller 101 controls a movement mechanism (not shown) that changes at least one of the position of the light source 10 or the orientation of the light source 10 to change at least one of a relative position of the light source 10 to the iris aperture 21 and the slit 22, and a relative orientation of the light source 10 to the iris aperture 21 and the slit 22.

The movement mechanism 22D includes an actuator, and moves the slit 22 in the optical axis direction of the illumination optical system 20 under the control from the main controller 101. The main controller 101 controls the movement mechanism 22D in accordance with the state of the subject's eye E to arrange the slit 22 at the position corresponding to the state of the subject's eye E. Examples of the state of the subject's eye E include a shape of the fundus Ef, a dioptric power (diopter scale), and an axial length. The dioptric power, for example, can be identified from the position on the optical axis of the focusing lens 47 when it is determined to be in the focused state by the focus control using the focus indicator optical system and the focusing lens 47. Alternatively, the dioptric power can be acquired from a known eye refractive power measurement apparatus as disclosed in Japanese Unexamined Patent Application No. 61-293430 or Japanese Unexamined Patent Application Publication No. 2010-259495, for example. The axial length can be obtained from a known axial length measurement apparatus or a measurement value acquired by an optical coherence tomography.

For example, the storage unit 102 stores first control information. In the first control information, the positions of the slit 22 on the optical axis of the illumination optical system 20 are associated with the dioptric powers in advance. The main controller 101 identifies the position of the slit 22 corresponding to the dioptric power by referring to the first control information, and controls the movement mechanism 22D so as to arrange the slit 22 at the identified position.

Here, as the slit 22 moves, the light amount distribution of the light passing through the aperture formed in the slit 22 changes. In this case, as described above, the main controller 101 can control the movement mechanism to change at least one of the position of the light source 10 or the orientation of the light source 10.

Examples of the control for the optical scanner 30 include a control of the scan range (scan start position and scan end position), the scan speed, and the deflection operation. Examples of the deflection operation include one-dimensional and two-dimensional deflection operations.

Examples of the control for the imaging optical system 40 include control for a movement mechanism 47D (focus control). The movement mechanism 47D includes an actuator, and moves the focusing lens 47 in the optical axis direction of the imaging optical system 40, under the control from the main controller 101. The main controller 101 can control the movement mechanism 47D based on an analysis result of the image acquired using the image sensor 51. For example, when performing focus adjustment, the main controller 101 controls the focus indicator optical system to project split indicator light as the focus indicator light onto the fundus Ef of the subject's eye E, identifies the two split indicator images depicted in the image acquired using the image sensor 51, and controls the movement mechanism 47D according to the Schemer principle from the positional relationship between the identified two split indicator images. In some embodiments, without using the focus indicator optical system, the main controller 101 analyzes the image acquired using the image sensor 51 to identify whether or not it is in the focused state, and controls the movement mechanism 47D according to the identified focused state. Further, the main controller 101 can control the movement mechanism 47D based on an operation content of the user using an operation unit 110 described below.

Examples of the control for the imaging device 50 include control for the image sensor 51 (rolling shutter control). Examples of the control for the image sensor 51 include the reset control, the exposure control, the charge transfer control, and the output control. Further, time required for the reset control, time (exposure time) required for the exposure control, time required for the charge transfer control, and time required for the output control, etc., can be changed.

When the ophthalmic apparatus 1 is provided with the focus indicator optical system, the main controller 101 can control the focus indicator optical system. Examples of the control for the focus indicator optical system include control for the focus indicator light source, and control for coupling the optical path from the focus indicator optical system with the optical path of the illumination optical system 20.

Examples of the control for the anterior segment cameras 60A and 60B include control for light receiving sensitivity of each camera, control for the frame rate (light receiving timing), and synchronization control of the anterior segment cameras 60A and 60B.

The movement mechanism 150 three-dimensionally moves at least the optical system of the apparatus of the ophthalmic apparatus 1 (illumination optical system 20 and the imaging optical system 40), for example. In a typical example, the movement mechanism 150 includes a mechanism for moving at least the optical system (body for housing the optical system) in the X direction (left-right direction), a mechanism for moving it in the Y direction (up-down direction), and a mechanism for moving it in the Z direction (depth direction, front-back direction, working distance direction). The mechanism for moving in the X direction includes an X stage movable in the X direction and an X movement mechanism for moving the X stage, for example. The mechanism for moving in the Y direction includes a Y stage movable in the Y direction and a Y movement mechanism for moving the Y stage, for example. The mechanism for moving in the Z direction includes a Z stage movable in the Z direction and a Z movement mechanism for moving the Z stage, for example. Each movement mechanism includes a pulse motor as an actuator and operates under the control from the main controller 101.

The control for the movement mechanism 150 is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement.

In the case of manual alignment, a user operates the operation unit 110 to relatively move the optical system and subject's eye E so as to cancel the displacement of the subject's eye E relative to the optical system. For example, the main controller 101 controls the movement mechanism 150 to relatively move the optical system with respect to the subject's eye E, by outputting a control signal corresponding to the operation content for the operation unit 110 to the movement mechanism 150.

In the case of automatic alignment, the main controller 101 controls the movement mechanism 150 to relatively move the optical system relative to the subject's eye E so as to cancel the displacement of the subject's eye E relative to the optical system. Specifically, the main controller 101 performs arithmetic processing using a trigonometry based on the positional relationship between the anterior segment cameras 60A and 60B and the subject's eye E, and controls the movement mechanism 150 so that the positional relationship of the subject's eye E relative to the optical system becomes a predetermined relationship, as described in Japanese Unexamined Patent Application Publication No. 2013-248376.

Examples of the control for the data processor 200 include various kinds of image processing and various kinds of analysis processing on the light receiving results acquired from the image sensor 51. Examples of the image processing include noise removal processing on the light receiving results, brightness correction processing for easily identifying a predetermined site depicted in the light receiving image based on the light receiving results. Examples of the analysis processing include the identification processing of the split indicator images for the focus control described above, the identification processing of the control result for the focusing lens 47 (movement mechanism 47D) according to the Scheiner principle, and the identification processing of the focused state. Examples of the identification processing of the control result for the focusing lens 47 include the identification processing of the position on the optical axis of the focusing lens 47. Examples of the identification processing of the focused state include the identification processing of the control result for the focusing lens 47 based on the image contrast, and the identification processing of the control result for the focusing lens 47 based on the brightness in the brightest region in the image.

The data processor 200 can form the light receiving image corresponding to the arbitrary opening range based on the light receiving result(s) read out from the image sensor 51 using the rolling shutter method, under the control from the main controller 101 (controller 100). The data processor 200 can sequentially form light receiving light images corresponding to the opening ranges and can form an image of the subject's eye E from a plurality of formed light receiving images.

The data processor 200 includes a processor, and realizes the above functions by performing processing corresponding to the program(s) stored in the storage unit or the like.

(Storage Unit 102)

The storage unit 102 stores various computer programs and data. The computer programs include an arithmetic program and a control program for controlling the ophthalmic apparatus 1.

(Operation Unit 110)

The operation unit 110 includes an operation device or an input device. The operation unit 110 includes buttons and switches (e.g., operation handle, operation knob, etc.) and operation devices (e.g., mouse, keyboard, etc.) provided in the ophthalmic apparatus 1. In addition, the operation unit 110 may include any operation device or any input device, such as a trackball, a control panel, a switch, a button, a dial, etc.

(Display Unit 120)

The display unit 120 displays the image of the subject's eye E generated by data processor 200. The display unit 120 is configured to include a display device such as a flat panel display such as an LCD (Liquid Crystal Display). In addition, the display unit 120 may include various types of display devices such as a touch panel and the like provided in the body of the ophthalmic apparatus 1.

It should be noted that the operation unit 110 and the display unit 120 do not need to be configured to be separate devices. For example, a device like a touch panel, which has a display function integrated with an operation function, can be used. In this case, the operation unit 110 includes the touch panel and a computer program. The operation content for the operation unit 110 is fed to the controller 100 as electrical signal(s). Moreover, operations and inputs of information may be performed using a graphical user interface (GUI) displayed on the display unit 120 and the operation unit 110. In some embodiments, the functions of the display unit 120 and the operation unit 110 are realized a touch screen.

(Example of Configuration of Data Processor 200)

Figure 4:
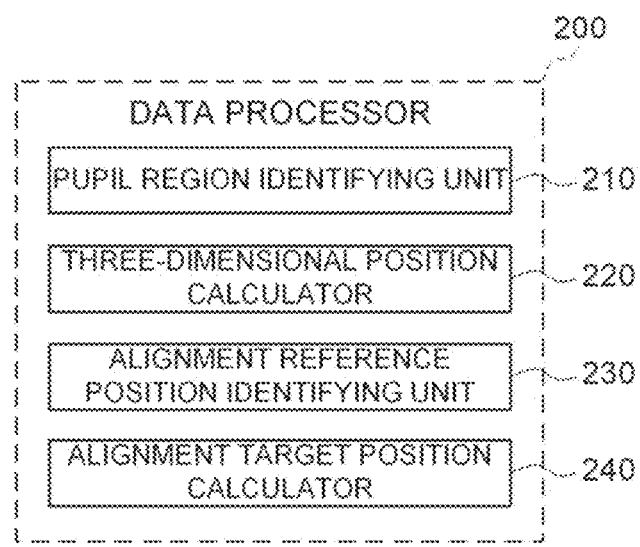
FIG. 4 is a functional block diagram illustrating an example of a configuration of a control system of the ophthalmic apparatus according to the first embodiment.

FIG. 4 shows a functional block diagram of an example of the configuration of the data processor 200 in FIG. 3.

The data processor 200 includes a pupil region identifying unit 210, a three-dimensional position calculator 220, an alignment reference position identifying unit 230, and an alignment target position calculator 240.

(Pupil Region Identifying Unit 210)

The pupil region identifying unit 210 identifies a pupil region (center position, position of the center of gravity) in the anterior segment image corresponding to the pupil of the anterior segment Ea, by analyzing each of a pair of the anterior segment images (photographic images) obtained by the anterior segment cameras 60A and 60B.

First, the pupil region identifying unit 210 identifies the image region (pupil region) corresponding to the pupil of the subject's eye E based on the distribution of pixel values (luminance values etc.) in the anterior segment image. Generally, the pupil is represented with lower luminance compared to other sites, and therefore, the pupil region may be identified by searching an image region with low luminance. In this case, the pupil region may be identified by taking the shape of the pupil into consideration. That is, it is possible to configure such that the pupil region is identified by searching for a substantially circular image region with low luminance.

Next, the pupil region identifying unit 210 identifies the center position of the identified pupil region. As described above, the pupil is substantially circular; therefore, it is possible to identify the contour of the pupil region, to identify the center position of this contour (an approximate circle or an approximate ellipse thereof), and to treat this as the pupil center position. Instead, by obtaining the center of gravity of the pupil region, this position may be used as the position of the center of gravity of the pupil.

The pupil region identifying unit 210 can sequentially identify the pupil regions corresponding to the pupil for the pair of the anterior segment images sequentially obtained by the anterior segment cameras 60A and 60B. Moreover, the pupil region identifying unit 210 may identify the pupil regions every one or more arbitrary number of frames for the pair of the anterior segment images sequentially obtained by the anterior segment cameras 60A and 60B.

(Three-Dimensional Position Calculator 220)

The three-dimensional position calculator 220 calculates a three-dimensional position of the pupil based on the positions of the anterior segment cameras 60A and 60B and the pupil region (center position) identified by the pupil region identifying unit 210. The three-dimensional position calculator 220 calculates the three-dimensional position of the subject's eye E (pupil) by applying a known trigonometry to the positions of the two anterior segment cameras 60A and 60B (these are known) and the position corresponding to the pupil region in the pair of the anterior segment images, as disclosed in Japanese Unexamined Patent Application Publication No. 2013-248376.

(Alignment Reference Position Identifying Unit 230)

The alignment reference position identifying unit 230 identifies an alignment reference position (Xr, Yr, Zr) on the optical axis of the imaging optical system 40 for the optical system (imaging optical system 40) in the ophthalmic apparatus 1. The alignment reference position (Xr, Yr, Zr) is a three-dimensional position defined in a three-dimensional coordinate system with the origin at a predetermined reference position in the optical system of the ophthalmic apparatus 1. The coordinate position Xr in the X direction and the coordinate position Yr in the Y direction of the alignment reference position are the positions on the XY plane where the optical axis of the imaging optical system 40 coincides with the axis of the subject's eye E. The coordinate position Zr in the Z direction of the alignment reference position is the position on the optical axis of the imaging optical system 40 where the distance from the imaging optical system 40 to the subject's eye becomes a predetermined working distance. Here, the working distance is a preset value which is called a working distance of the objective lens 46, and it means the distance between the subject's eye E and the optical system when measuring (imaging) using the imaging optical system 40.

Examples of the alignment reference position include a corneal apex position of the subject's eye E. In this case, the alignment reference position identifying unit 230 can identify the alignment reference position based on the three-dimensional position of the pupil region identified by the three-dimensional position calculator 220 and intraocular parameter(s). Examples of the intraocular parameter(s) include a distance in the optical axis direction of the imaging optical system 40 from the corneal apex position to the pupil. The distance in the optical axis direction of the imaging optical system 40 from the corneal apex position to the pupil may be a value calculated from parameter of a known schematic eye, or may be a measured value of the subject's eye E. The alignment reference position identifying unit 230 can obtain the alignment reference position from the three-dimensional position of the pupil region calculated by the three-dimensional position calculator 220, using the intraocular parameter representing the distance in the optical axis direction of the imaging optical system 40 from the corneal apex position to the pupil.

(Alignment Target Position Calculator 240)

The alignment target position calculator 240 calculates an alignment target position based on the alignment reference position identified by the alignment reference position identifying unit 230. The alignment target position is the alignment position at which the light amount passing through the imaging aperture 49 is less than when the subject's eye E is placed at the alignment reference position.

Here, the corneal curvature radius of the subject's eye is assumed to be R. In this case, when the subject's eye E is illuminated with the illumination light, the cornea acts as a reflective surface with a corneal curvature radius R. As a result, a corneal reflection image (Purkinje image) is formed at a position (position Pp in FIG. 1) that is (R/2) away from the corneal apex position in the optical axis direction of the imaging optical system 40. In contrast, the imaging aperture conjugate position (position Pa in FIG. 1), which is substantially conjugate position optically to the imaging aperture 49, is located near the pupil or the corneal apex, in the focused state.

In this case, a distance (gap length) in the optical axis direction of the imaging optical system 40 from the corneal apex position to the imaging aperture conjugate position Pa is assumed to be d. The alignment target position calculator 240 calculates the alignment target position such that the light amount of the returning light passing through the imaging aperture 49 is less than when the distance in the optical axis direction of the imaging optical system 40 between the imaging aperture conjugate position Pa and the position Pp of the corneal reflection image is (R/2−d).

Specifically, the alignment target position calculator 240 calculates the alignment target position (Xr, Yr, Zr+Δs) shifted by a shift amount Δs from the alignment reference position (Xr, Yr, Zr) in the Z direction (the working distance direction, working distance direction approaching the fundus Ef in FIG. 1). Here, the shift amount Δs is a predetermined value that is uniquely defined by the optical arrangement of the optical systems (illumination optical system 20, optical scanner 30, and imaging optical system 40) of the ophthalmic apparatus 1. This allows to calculate the alignment target position, which is shifted by a component in the Z direction, relative to the alignment reference position. Here, the shift amount Δs is determined so that (R/2−d+Δs) is equal to or greater than a predetermined gap threshold Gp.

The main controller 101 controls the movement mechanism 150 so as to arrange the subject's eye E at the alignment target position calculated by the alignment target position calculator 240. In other words, the main controller 101 controls the movement mechanism 150 so that the light amount of the returning light passing through the imaging aperture 49 becomes less than when the distance in the optical axis direction of the imaging optical system 40 between the imaging aperture conjugate position Pa and the position Pp of the corneal reflection image is (R/2−d). For example, the main controller 101 controls the movement mechanism 150 so that the distance in the optical axis direction of the imaging optical system 40 between the imaging aperture conjugate position Pa and the position Pp of the corneal reflection image is equal to or greater than the predetermined gap threshold Gp.

It should be noted that the refractive power in the optical path of the illumination light is dominated by the influence of the cornea, so the illumination light entering the cornea does not have to be collimated. Even in this case, the occurrence of flare caused by the corneal reflection light can be suppressed, by reducing the light amount of the returning light passing through the imaging aperture 49 with reference to when the distance in the optical axis direction of the imaging optical system 40 between the imaging aperture conjugate position Pa and suppress position Pp of the corneal reflection image is (R/2−d).

Further, by adjusting the shift amount Δs in advance, the degradation of the fundus image quality can be substantially suppressed even when the light amount of the returning light passing through the imaging aperture 49 is reduced.

This makes it possible to adjust the relative position of the optical system to the subject's eye with high precision so as to suppress the occurrence of flare, without analyzing the fundus images in advance or unnecessarily moving the optical system. As a result, the occurrence of flare included in the fundus images can be suppressed with high precision using a simple configuration, while suppressing the degradation of fundus image quality.

(Other Configurations)

In some embodiments, the ophthalmic apparatus 1 further includes a fixation projection system. For example, an optical path of the fixation projection system is coupled with the optical path of the imaging optical system 40 in the configuration of the optical system shown in FIG. 1. The fixation projection system can present internal fixation targets or external fixation targets to the subject's eye E. In case of presenting the internal fixation target to the subject's eye E, the fixation projection system includes an LCD that displays the internal fixation target under the control from the controller 100, and projects a fixation light flux output from the LCD onto the fundus Ef of the subject's eye E. The LCD is configured to be capable of changing the display position of the fixation target on the screen of the LCD. By changing the display position of the fixation target on the screen of the LCD, the projected position of the fixation target on the fundus of the subject's eye E can be changed. The display position of the fixation target on the LCD can be designated using the operation unit 110 by the user.

[Operation]

Next, the operation of the ophthalmic apparatus 1 will be described.

Figure 5:
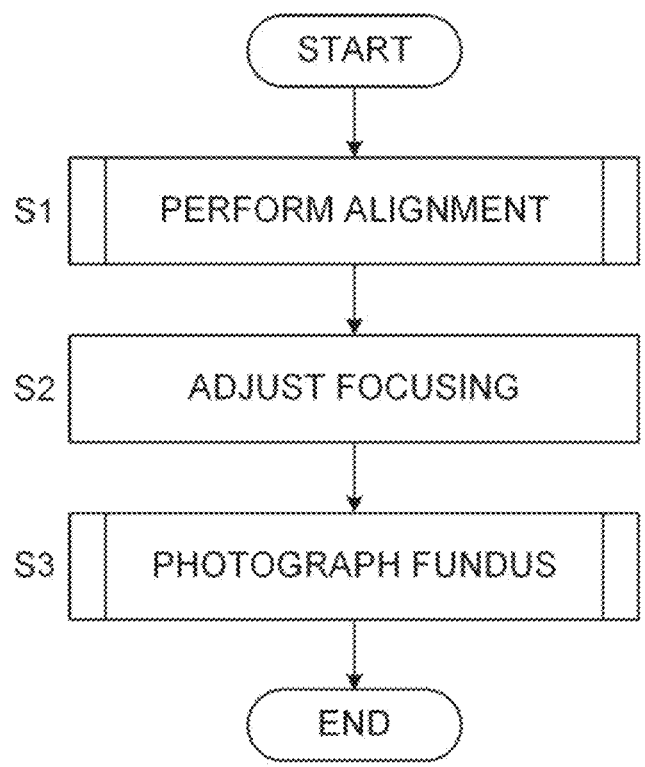
FIG. 5 is a flow chart illustrating an example of an operation of the ophthalmic apparatus according to the first embodiments.
Figure 6:
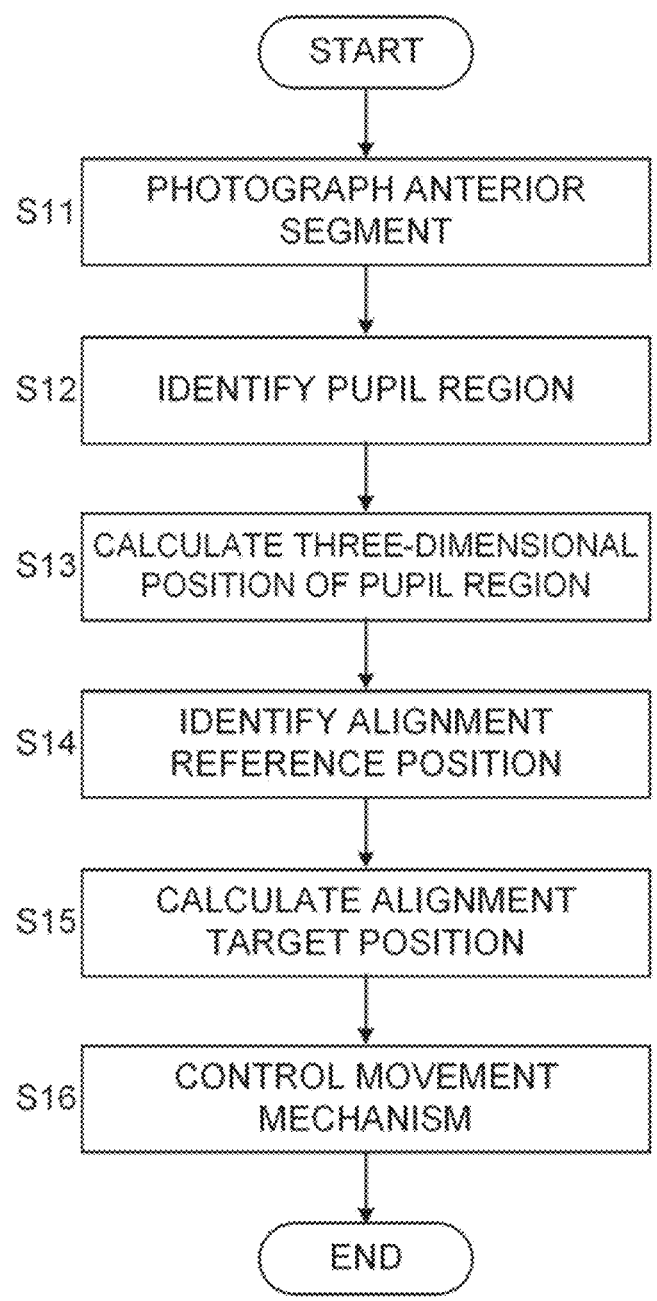
FIG. 6 is a flow chart illustrating an example of an operation of the ophthalmic apparatus according to the first embodiments.
Figure 7:
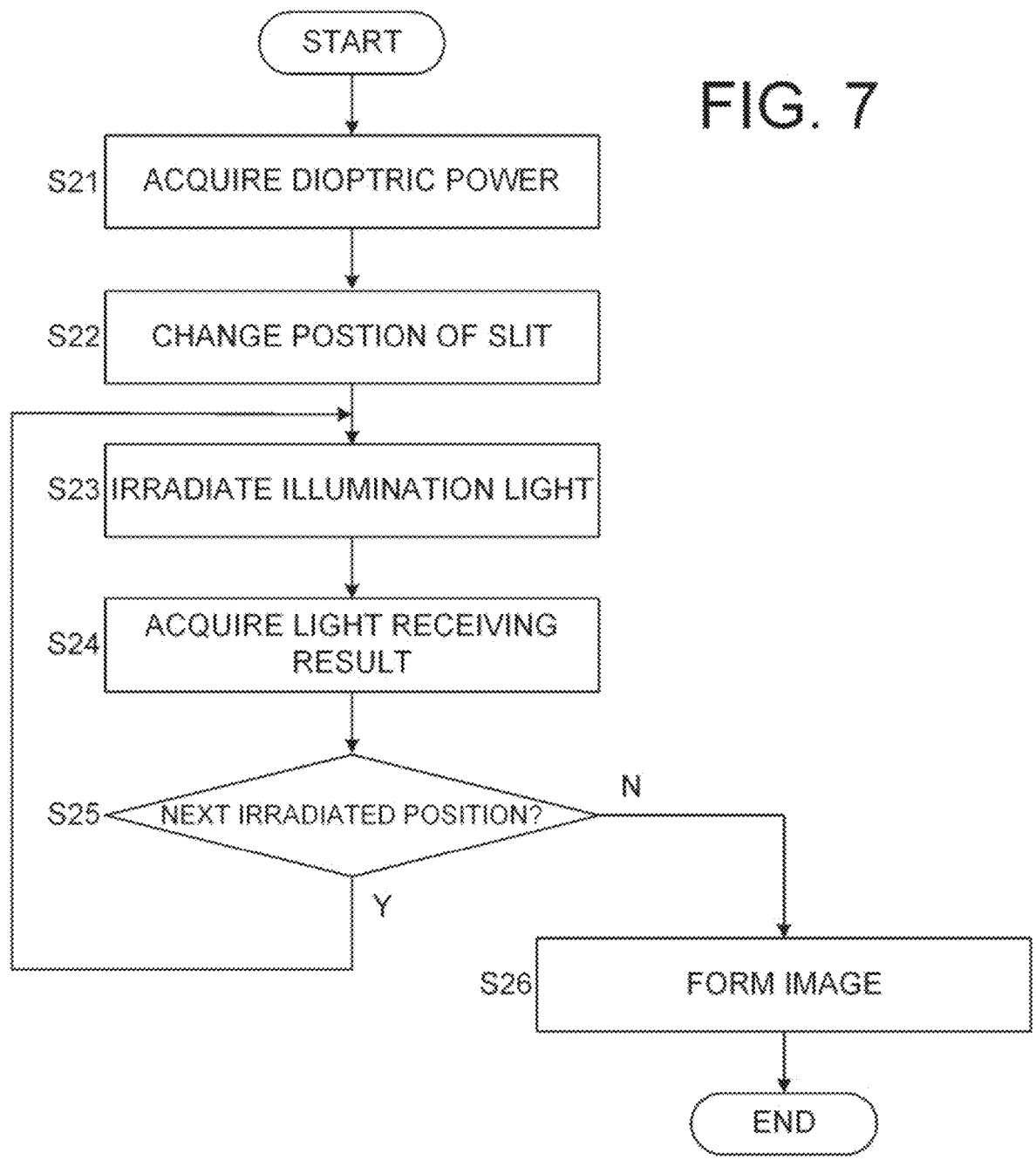
FIG. 7 is a flow chart illustrating an example of an operation of the ophthalmic apparatus according to the first embodiments.

FIGS. 5 to 7 show flow charts of examples of the operation of the ophthalmic apparatus 1 according to the first embodiment. The storage unit 102 stores computer programs for realizing the processing shown in FIGS. 5 to 7. The main controller 101 operates according to the computer programs, and thereby the main controller 101 performs the processing shown in FIGS. 5 to 7.

FIG. 5 represents a flow chart of an example of the operation of the ophthalmic apparatus 1. FIG. 6 shows a flow chart of an example of the operation of step S1 in FIG. 5. FIG. 7 shows a flow chart of an example of the operation of step S3 in FIG. 5.

(S1: Perform Alignment)

First, the main controller 101 performs alignment. As a result, the position matching of the optical system relative to the subject's eye E is completed in a state where the light amount passing through the imaging aperture 49 is less than when the distance in the optical axis direction of the imaging optical system 40 between the imaging aperture conjugate position Pa and the position Pp of the corneal reflection image is (R/2−d). The details of step S1 will be described below.

(S2: Adjust Focusing)

Next, the main controller 101 controls the movement mechanism 47D to move the focusing lens 47 in the optical axis direction to perform focus adjustment.

For example, the main controller 101 controls the focus indicator optical system not shown in the figure to project the split indicator light as the focus indicator light onto the fundus Ef of the subject's eye E. And then, the main controller 101 controls the data processor 200 to identify the two split indicator images depicted in the image acquired using the image sensor 51. The main controller 101 controls the movement mechanism 47D according to the Scheiner principle from the positional relationship between the identified two split indicator images.

For example, without using the focus indicator optical system, the main controller 101 may control the data processor 200 to analyze the image acquired using the image sensor 51 to identify the focused state. In this case, the main controller 101 controls the movement mechanism 47D in accordance with the identified focused state.

For example, the user may operate the operation unit 110 to change the focused state while referring to the fundus image displayed on the display unit 120. In this case, the main controller 101 controls the movement mechanism 47D based on the operation content of the user using the operation unit 110.

(S3: Photograph Fundus)

Next, the main controller 101 controls the illumination optical system 20, the optical scanner 30, the imaging optical system 40, and the imaging device 50 to photograph the fundus Ef of the subject's eye E, and acquires the fundus image. The details of step S3 will be described below.

This terminates the operation of the ophthalmic apparatus 1 (END).

Step S1 in FIG. 5 is performed according to the flow shown in FIG. 6.

(S11: Photograph Anterior Segment)

First, the main controller 101 controls the anterior segment cameras 60A and 60B to start photographing the anterior segment Ea of the subject's eye E from different directions, and starts acquiring a pair of anterior segment images acquired substantially simultaneously.

(S12: Identify Pupil Region)

Next, the main controller 101 controls the pupil region identifying unit 210 to identify the pupil region for each of the pair of anterior segment images acquired in step S11.

(S13: Calculate Three-Dimensional Position of Pupil Region)

Next, the main controller 101 controls the three-dimensional position calculator 220 to calculate the three-dimensional position of the pupil region using the pair of anterior eye images identified in step S12, as described above.

(S14: Identify Alignment Reference Position)

Subsequently, the main controller 101 controls the alignment reference position identifying unit 230 to identify the corneal apex position as the alignment reference position from the three-dimensional position of the pupil region calculated in step S13 and the intraocular parameter, as described above.

(S15: Calculate Alignment Target Position)

Subsequently, the main controller 101 controls the alignment target position calculator 240 to calculate the alignment target position shifted by a predetermined shift amount Δs in the optical axis direction of the imaging optical system 40 with reference to the alignment reference position identified in step S14.

(S16: Control Movement Mechanism)

Next, the main controller 101 controls the movement mechanism 150 to arrange the subject's eye E at the alignment target position calculated in step S15.

This terminates the processing of step S1 in FIG. 5 (END).

Step S3 in FIG. 5 is performed according to the flow shown in FIG. 7.

(S21: Acquire Dioptric Power)

First, the main controller 101 acquires the dioptric power. For example, the main controller 101 identifies the dioptric power from the position on the optical axis of the focusing lens 47 having been set to the focused state (or the control result for the actuator that moves the movement mechanism 47D). The main controller 101 may acquire the dioptric power of the subject's eye E from the external ophthalmic measurement apparatus or the electronic medical record.

(S22: Change Position of Slit)

Next, the main controller 101 changes the position of the slit 22 on the optical axis of the illumination optical system 20 in accordance with the dioptric power of the subject's eye E acquired in step S21.

Specifically, the main controller 101 specifies the position of the slit 22 corresponding to the dioptric power by referring to the first control information stored in the storage unit 102, and controls the movement mechanism 22D so as to arrange the slit 22 at the identified position.

(S23: Irradiate Illumination Light)

Next, the main controller 101 controls the illumination optical system 20 to generate the slit-shaped illumination light, and to start the deflection control of the optical scanner 30 to start irradiating the illumination light onto a desired irradiated region on the fundus Ef. When the irradiation of the illumination light is started, the slit-shaped illumination light is sequentially irradiated within the desired irradiated range as described above.

(S24: Acquire Light Receiving Result)

The main controller 101 acquires the light receiving result(s) of the pixels in the opening range of the image sensor 51 corresponding to the irradiated range of the illumination light on the fundus Ef performed in step S23, as described above.

(S25: Next Irradiated Position?)

The main controller 101 determines whether or not the next irradiated position is to be irradiated with the illumination light. The main controller 101 can determine whether or not the next irradiated position is to be irradiated with the illumination light, by determining whether or not the irradiated range of the illumination light that is moved sequentially has covered a predetermined imaging range of the fundus Ef.

When it is determined that the next irradiated position is to be irradiated with the illumination light (step S25: Y), the operation of the ophthalmic apparatus 1 proceeds to step S23. When it is determined that the next irradiated position is not to be irradiated with the illumination light (step S25: N), the operation of the ophthalmic apparatus 1 proceeds to step S26.

(S26: Form Fundus Image)

In step S25, when it is determined that the next irradiated position is not to be irradiated with the illumination light (step S25: N), the main controller 101 controls the data processor 200 to form the image of the subject's eye E from the light receiving results acquired repeatedly while changing the irradiated range of the illumination light in steps S23 and S24.

For example, the data processor 200 syntheses a plurality of light receiving results with different irradiated ranges (opening ranges on the light receiving surface SR of the image sensor 51) of the illumination light for the number of times repeating the process in steps S23 to S25, based on the order of the movement of the irradiated range. Thereby, the fundus image of the fundus Ef for one frame is formed.

In some embodiments, in step S23, the illumination light is irradiated on the irradiated range set so as to have an overlapping region with the adjacent irradiated range. Thereby, in step S26, the fundus image for one frame is formed by synthesizing the overlapping regions so as to overlap with each other.

This terminates the processing of step S3 in FIG. 5 (END).

Figure 8:
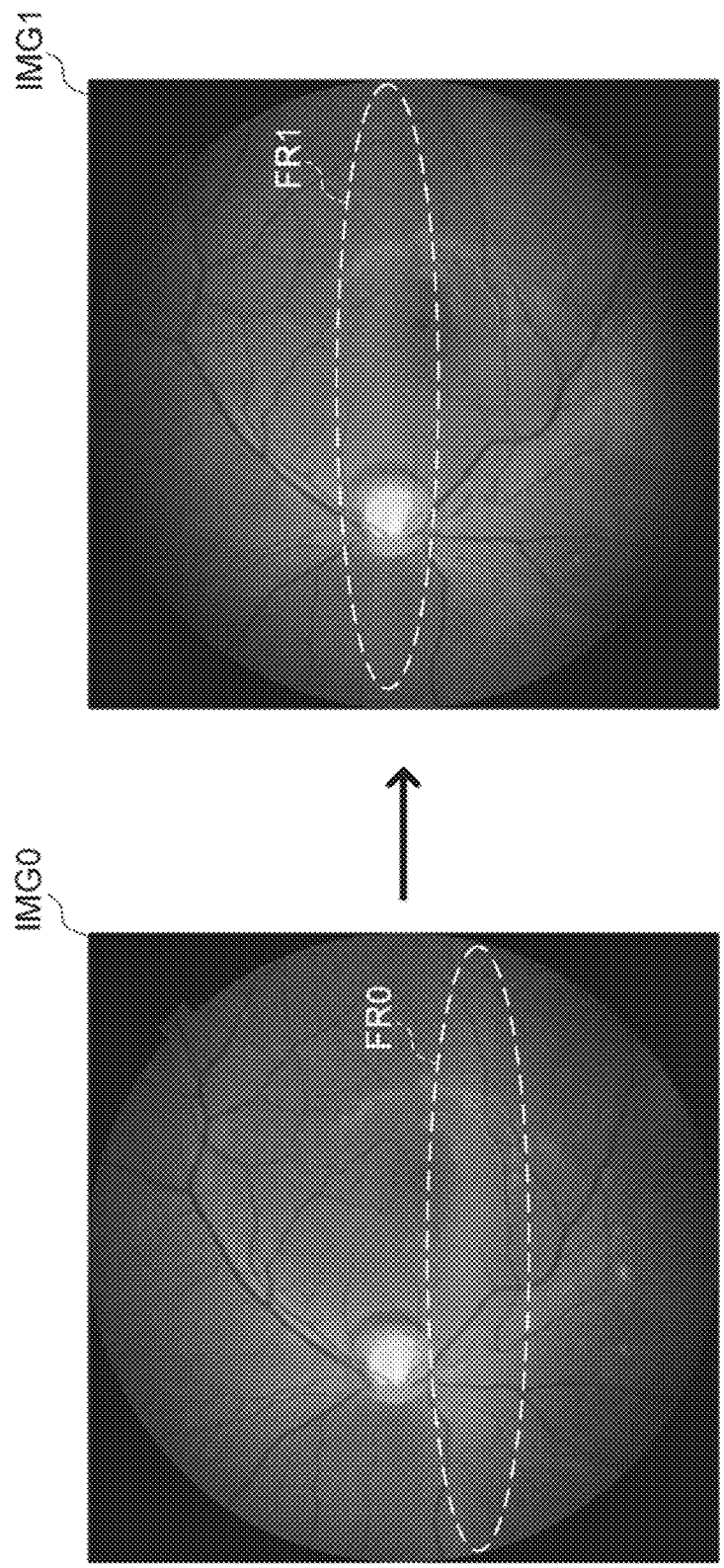
FIG. 8 is a schematic diagram for explaining an operation of the ophthalmic apparatus according to the first embodiment.

FIG. 8 shows a diagram describing the operation of the ophthalmic apparatus 1 according to the first embodiment. FIG. 8 represents the fundus image IMG0 when the optical system is performed position matching of the optical system relative to the subject's eye based on the alignment reference position and the fundus image IMG1 when the optical system is performed position matching of the optical system relative to the subject's eye E based on the alignment target position.

In the fundus image IMG0, a flare FR0 extending in the X direction (corresponding to the slit direction on the fundus Ef) occurs on the fundus Ef. By performing position matching of the optical system relative to the subject's eye E for the alignment target position, the light amount of the returning light of the illumination light passing through the imaging aperture 49 is reduced. Therefore, in the fundus image IMG1, compared to the flare FR0, the degradation of image quality due to a flare FR1 can be suppressed.

It should be noted that, in the fundus image IMG1, optical condition(s) in the optical system is/are changed by performing position matching for the alignment target position and that the location of the occurrence of flare is different compared to the fundus image IMG0.

In some embodiments, the alignment target position is calculated so that the location of the occurrence of flare in the fundus image does not overlap with a region of interest. For example, in case of FIG. 8, the alignment target position is calculated so that the location of the occurrence of flare moves near the upper or lower edge of the fundus image. In this case, the shift amount Δs should be a predetermined value adjusted in advance.

In some embodiments, the shift amount Δs may be changed in accordance with the position within the irradiated range on the fundus Ef by the optical scanner 30. In this case, the reduction in the light amount passing through the imaging aperture 49 can be minimized.

As described above, according to the first embodiment, the alignment target position that is shifted in the optical axis direction of the imaging optical system 40 by a predetermined amount from the alignment reference position is calculated so that the light amount of the returning light passing through the imaging aperture 49 is less than when the distance in the optical axis direction of the imaging optical system 40 between the imaging aperture conjugate position Pa and the position Pp of the corneal reflection image is (R/2−d). Thereby, the position matching of the optical system relative to the subject's eye E is performed using the calculated alignment target position, without analyzing the fundus image(s). As a result, it is possible to adjust the relative position of the optical system to the subject's eye with high precision so as to suppress the occurrence of flare, without necessarily moving the optical system. As a result, the occurrence of flare included in the fundus images can be suppressed with high precision using a simple configuration, while suppressing the degradation of fundus image quality.

Second Embodiment

In the first embodiment, the case has been described where the alignment reference position (alignment target position) is calculated from the three-dimensional position of the pupil region identified based on the pair of anterior segment images acquired substantially simultaneously. However, the configuration of the ophthalmic apparatus according to the embodiments is not limited to this. In a second embodiment, the corneal apex position of the subject's eye E is measured, and the alignment target position is calculated using the corneal apex position, which is obtained by measurement, and the corneal curvature radius.

Hereinafter, a configuration and an operation of the ophthalmic apparatus according to the second embodiment will be described below mainly about the differences from the first embodiment.

Figure 9:
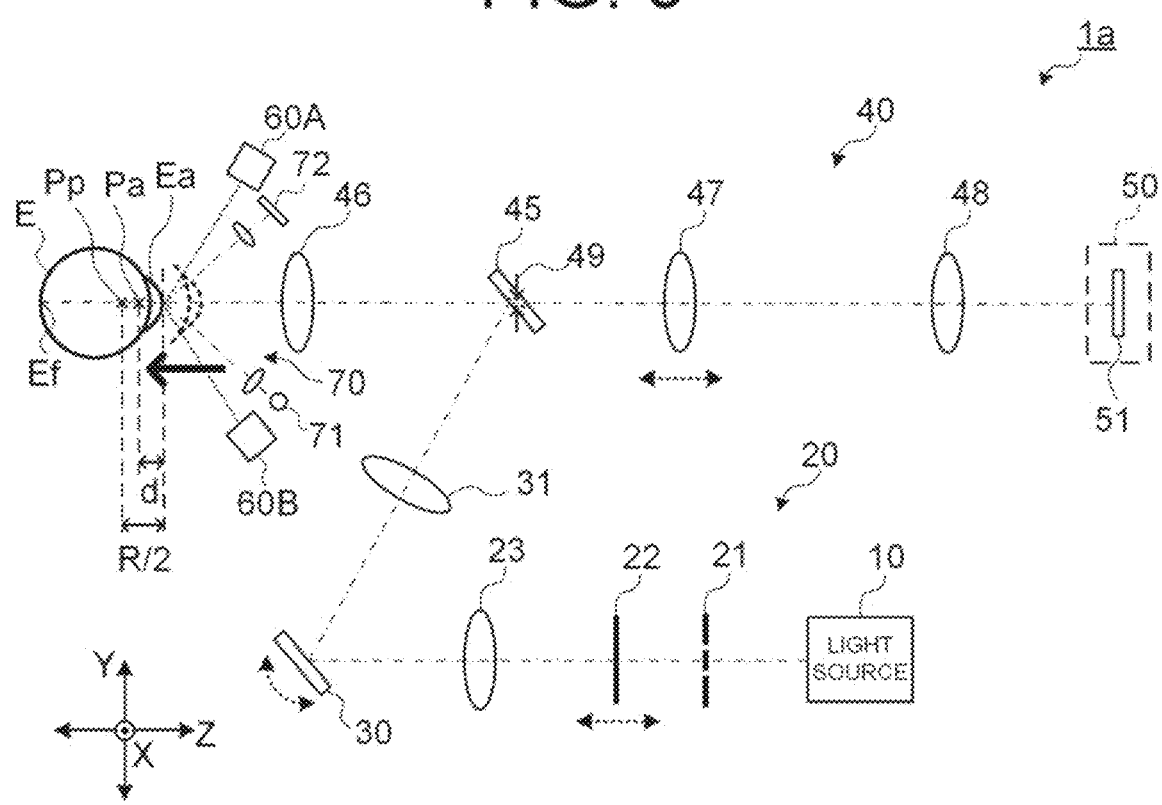
FIG. 9 is a schematic diagram illustrating an example of a configuration of an optical system of an ophthalmic apparatus according to a second embodiment.

FIG. 9 shows an example of a configuration of the optical system of the ophthalmic apparatus 1a according to the second embodiment. In FIG. 9, like reference numerals designate like parts as in FIG. 1, and the redundant explanation may be omitted as appropriate.

The optical system of the ophthalmic apparatus 1a has a configuration in which a corneal apex detection optical system 70 is added to the optical system of the ophthalmic apparatus 1 according to the first embodiment. The corneal apex detection optical system 70 is configured to detect the corneal apex of the subject's eye E.

The corneal apex detection optical system 70 includes a light source 71 and a line sensor 72. The light source 71 emits light in the visible region, the infrared region, or the near-infrared region from a position away from the optical axis of the imaging optical system 40 (optical system of the apparatus). The line sensor 72 is arranged at a position away from the optical axis of the imaging optical system 40 (optical system of the apparatus), and receives reflected light of the light from the light source 71 reflected on the anterior segment (specifically, corneal apex) of the subject's eye E.

On a light receiving surface of the line sensor 72, the received position of the reflected light changes in accordance with the relative position of the subject's eye E in the optical axis direction of the imaging optical system 40 to the optical system. Here, on the light receiving surface of the line sensor 72, the relative positions of the subject's eye E (specifically, corneal apex) in the optical axis direction of the imaging optical system 40 to the optical system are assigned corresponding to the received positions of the reflected light with reference to, for example, the alignment reference position. Therefore, from the received position of the reflected light on the light receiving surface of the line sensor 72, the relative position of the subject's eye E (corneal apex) in the optical axis direction of the imaging optical system 40 to the optical system can be identified.

Figure 10:
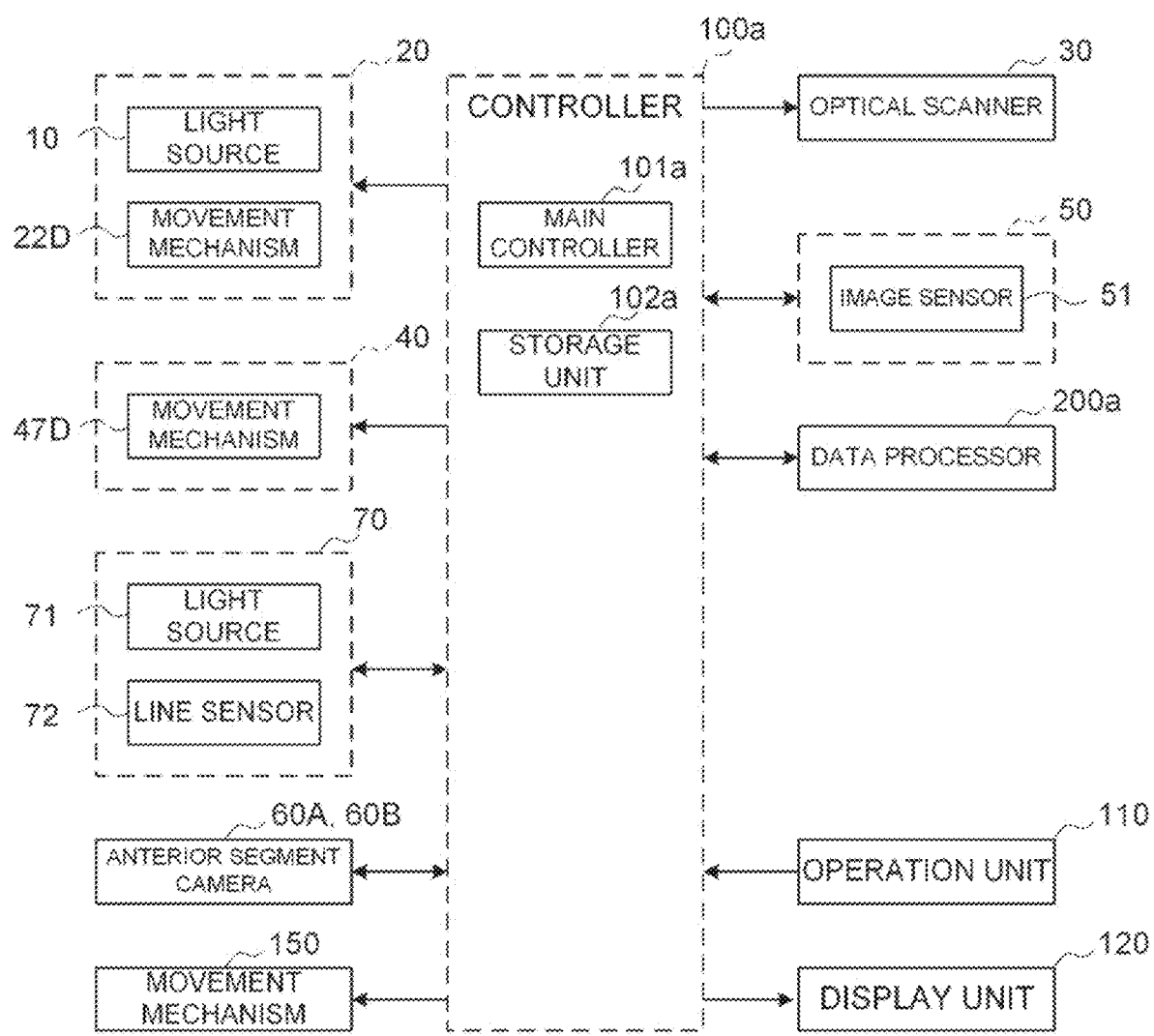
FIG. 10 is a functional block diagram illustrating an example of a configuration of a control system of the ophthalmic apparatus according to the second embodiment.

FIG. 10 shows a functional block diagram of an example of a configuration of the control system of the ophthalmic apparatus 1a according to the second embodiment. In FIG. 10, like reference numerals designate like parts as in FIG. 3 or FIG. 9. The same description may not be repeated.

The differences between the configuration of the control system of the ophthalmic apparatus 1a and that of the ophthalmic apparatus 1 according to the first embodiment are that a controller 100a is provided instead of the controller 100, and that the data processor 200a is provided instead of the data processor 200. In addition to the control performed by the controller 100, the controller 100a performs control for the corneal apex detection optical system 70 and controls the data processor 200a that calculates the alignment target position using a corneal detection position identified by the corneal apex detection optical system 70.

Figure 11:
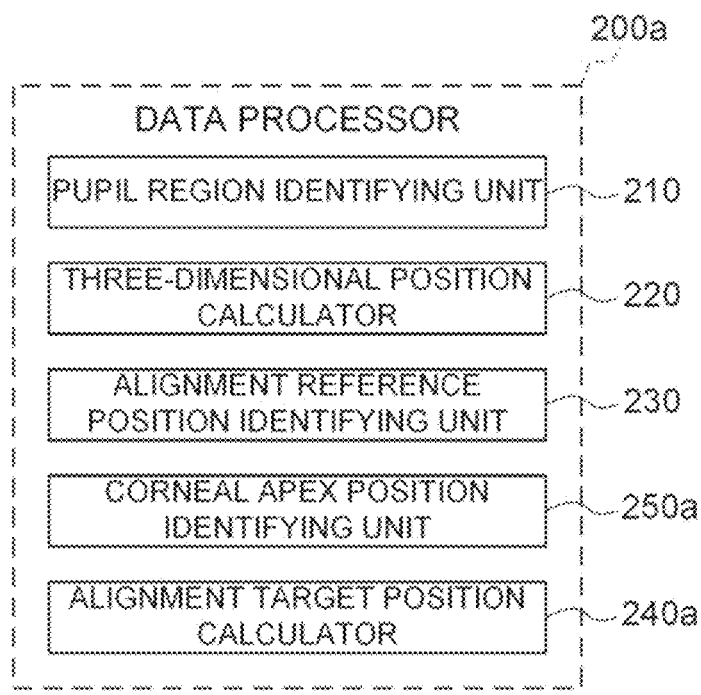
FIG. 11 is a functional block diagram illustrating an example of a configuration of a control system of the ophthalmic apparatus according to the second embodiment.

FIG. 11 shows a functional block diagram of an example of the configuration of the data processor 200a in FIG. 10. In FIG. 11, like reference numerals designate like parts as in FIG. 4, and the redundant explanation may be omitted as appropriate.

The data processor 200a includes the pupil region identifying unit 210, the three-dimensional position calculator 220, the alignment reference position identifying unit 230, a corneal apex position identifying unit 250a, and an alignment target position calculator 240a.

The corneal apex position identifying unit 250a identifies the relative position of the optical system in the optical axis direction of the imaging optical system 40 to the corneal apex of the subject's eye E, as described above. Here, the relative position corresponds to the received position of the reflected light of the light from the light source 71 on the light receiving surface of the line sensor 72. The positions in the three-dimensional coordinate system with the origin at a predetermined reference position in the optical system of the ophthalmic apparatus 1a is known. For example, the corneal apex position identifying unit 250a identifies the corneal apex position in the three-dimensional coordinate system from the relative position of the optical system in the optical axis direction of the imaging optical system 40 to the corneal apex of the subject's eye E. For example, the identified corneal apex position is used as the Z position (=Zr) of the alignment reference position identified by the alignment reference position identifying unit 230.

The alignment target position calculator 240a calculates the alignment target position (Xr, Yr, Zr+Δs1) from the alignment reference position (Xr, Yr. Zr) identified by the alignment reference position identifying unit 230. The alignment target position (Xr, Yr, Zr+Δs1) is a position shifted in the Z direction (working distance direction) by the shift amount Δs1 from the alignment reference position (Xr, Yr, Zr). Here, the shift amount Δs1 is a predetermined value that is uniquely defined by the optical arrangement of the optical systems in the ophthalmic apparatus 1a. In the second embodiment, a distance in the optical axis direction of the imaging optical system 40 from the corneal apex position identified by the corneal apex position identifying unit 250a to the imaging aperture conjugate position Pa is d, and the alignment target position, which is shifted by a component in the Z direction relative to the alignment reference position, is calculated using the corneal curvature radius R. Here, the shift amount Δs1 is determined so that (R/2−d+Δs1) is equal to or greater than a predetermined gap threshold Gp.

The operation of such ophthalmic apparatus 1a is almost the same as that of the ophthalmic apparatus 1 according to the first embodiment. However, the second embodiment differs from the first embodiment in that the corneal apex position detected using the corneal apex detection optical system 70 is used for calculating the alignment target position.

Figure 12:
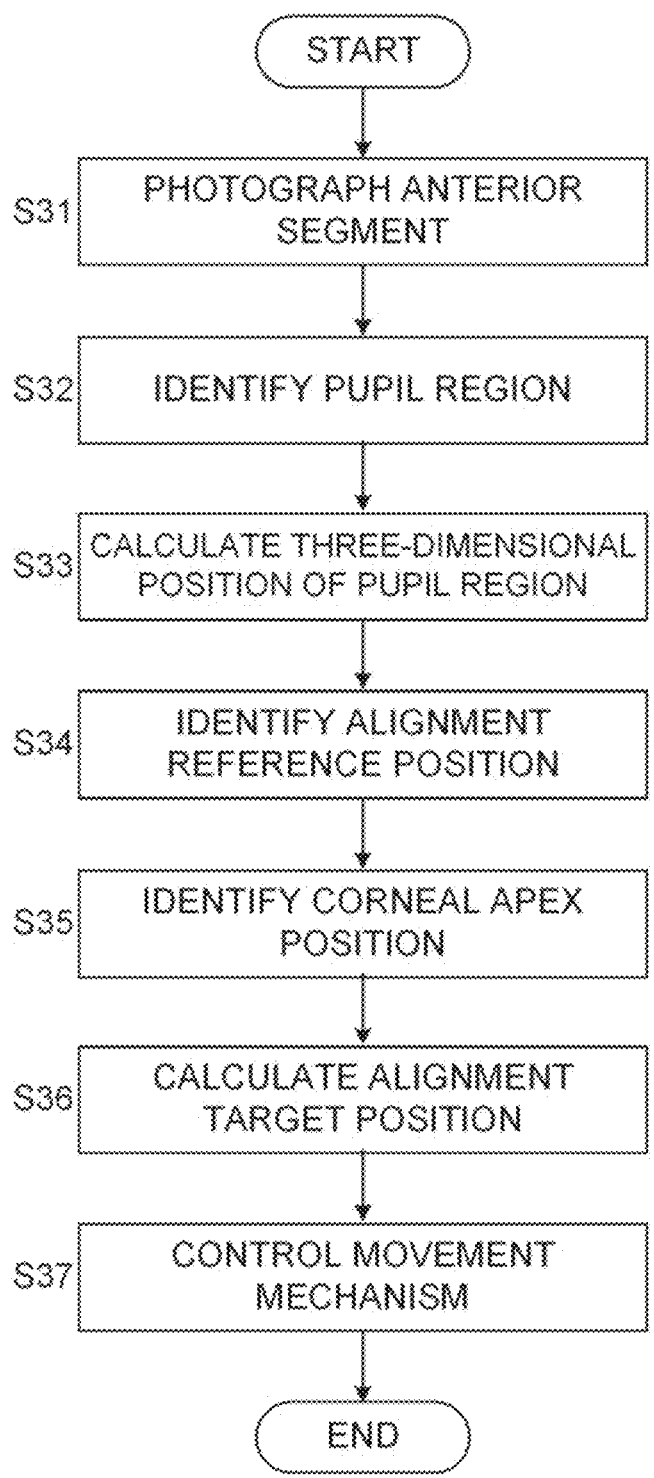
FIG. 12 is a flow chart of an example of an operation of the ophthalmic apparatus according to the second embodiment.

In the second embodiment, the processing in step S1 in FIG. 5 is performed according to the flow shown in FIG. 12.

FIG. 12 shows a flow chart of an example of the processing in step S1 in FIG. 5 according to the second embodiment. The storage unit 102a stores computer program(s) for realizing the processing shown in FIG. 12. The main controller 101a operates according to the computer programs, and thereby the main controller 101a performs the processing shown in FIG. 12.

(S31: Photograph Anterior Segment)
First, similar to step S11, the main controller 101a controls the anterior segment cameras 60A and 60B to start photographing the anterior segment Ea of the subject's eye E from different directions, and starts acquiring a pair of anterior segment images acquired substantially simultaneously.

(S32: Identify Pupil Region)
Next, similar to step S12, the main controller 101a controls the pupil region identifying unit 210 to identify the pupil region for each of the pair of anterior segment images acquired in step S31.

(S33: Calculate Three-Dimensional Position of Pupil Region)
Next, similar to step S13, the main controller 101a controls the three-dimensional position calculator 220 to calculate the three-dimensional position of the pupil region using the pair of anterior eye images identified in step S32, as described above.

(S34: Identify Alignment Reference Position)
Subsequently, similar to step S14, the main controller 101a controls the alignment reference position identifying unit 230 to identify the alignment reference position from the three-dimensional position of the pupil region calculated in step S33.

(S35: Identify Corneal Apex Position)
Subsequently, the main controller 101a causes the light from the light source 71 to irradiate the anterior segment of the subject's eye E using the corneal apex detection optical system 70, and to obtain the received position of the reflected light on the light receiving surface of the line sensor 72. The main controller 101a controls the corneal apex position identifying unit 250a to identify the corneal apex position of the subject's eye E from the obtained received position of the reflected light on the light receiving surface of the line sensor 72.

For example, the Z position of the alignment reference position identified in step S34 is replaced with the corneal apex position identified in step S35.

(S36: Calculate Alignment Target Position)
Subsequently, similar to step S15, the main controller 101a controls the alignment target position calculator 240a to calculate the alignment target position shifted by a predetermined shift amount Δs1 in the optical axis direction of the imaging optical system 40 with reference to the alignment reference position identified in steps S34 and S35.

(S37: Control Movement Mechanism)
Next, the main controller 101a controls the movement mechanism 150 to arrange the subject's eye E at the alignment target position calculated in step S36.

This terminates the processing of step S1 in FIG. 5 in the second embodiment (END).

According to such second embodiment, the corneal apex position of the subject's eye E is identified, and the alignment target position is calculated with reference to the alignment reference position. Here, the alignment target position is a position shifted by Δs1 in the optical axis direction of the imaging optical system 40, and Δs1 is determined based on the corneal apex position and the corneal curvature radius. This makes it possible to control the movement mechanism 150 so that the light amount of the returning light passing through the imaging aperture 49 is reduced with greater precision than in the first embodiment.

It should be noted that the case has been described where the X position and the Y position of the alignment reference position are obtained by analyzing the pair of anterior segment images acquired using the anterior segment cameras 60A and 60B in the second embodiment. However, the configuration of the ophthalmic apparatus according to the second embodiment is not limited to this. For example, the ophthalmic apparatus 1a may include an XY alignment system and obtain the X position and the Y position of the alignment reference position using the XY alignment system. In this case, the XY alignment system projects a bright spot (bright spot in the infrared region or near-infrared region) onto subject's eye E. The data processor 200a can, for example, acquire an anterior segment image of the subject's eye E using the anterior segment camera 60A, 60B, or the image sensor 51, and obtain the X position and the Y position of the alignment reference position based on the displacement between the bright spot image drawn on the acquired anterior segment image and a predetermined reference position.

As described above, according to the second embodiment, it is possible to adjust the relative position of the optical system to the subject's eye more precisely than in the first embodiment so that the occurrence of flare can be suppressed without unnecessarily moving the optical system. As a result, the occurrence of flare included in the fundus images can be suppressed with high precision using a simple configuration, while suppressing the degradation of fundus image quality.

Modification Example of Second Embodiment

The case has been described where the corneal apex position of the subject's eye E is detected, and the alignment reference position is calculated using the detected corneal apex position and the corneal curvature radius. However, the configuration according to the embodiments is not limited to this. According to a modification example of the second embodiment, a corneal reflection image position (Purkinje image position) of the illumination light is detected, and the alignment reference position is calculated using the detected corneal reflection image.

Hereinafter, the configuration and the operation of the ophthalmic apparatus according to the modification example of the second embodiment will be described, focused on the differences from the first embodiment.

The optical system of the ophthalmic apparatus according to the modification example of the second embodiment has a configuration in which a projection optical system (not shown) that projects light onto the subject's eye is added to the configuration of the optical system of the ophthalmic apparatus 1 according to the first embodiment. The control system of the ophthalmic apparatus according to the present modification example has a configuration in which a data processor 200b is provided instead of the data processor 200, in the configuration of the control system of the ophthalmic apparatus 1 according to the first embodiment.

Figure 13:
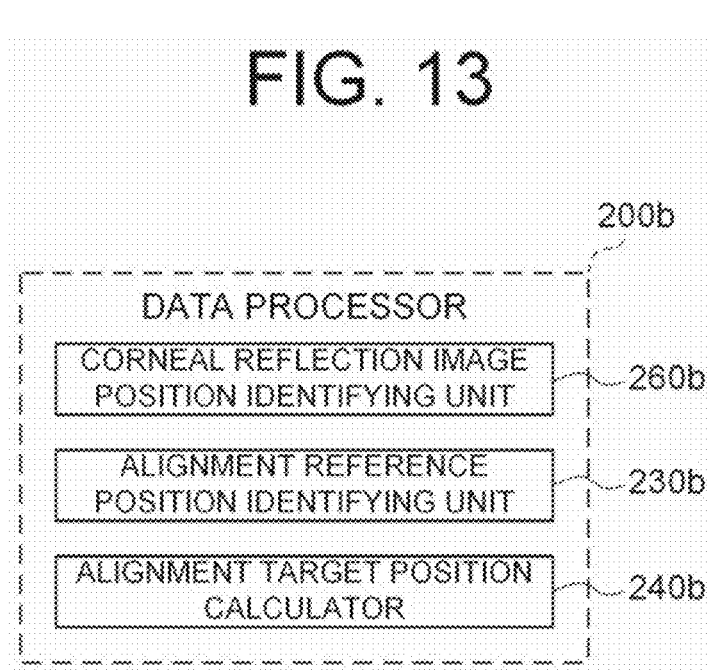
FIG. 13 is a functional block diagram of an example of a configuration of a control system of an ophthalmic apparatus according to a modification example of the second embodiment.

FIG. 13 shows a functional block diagram of an example of the configuration of the data processor 200b according to the present modification example. In FIG. 13, like reference numerals designate like parts as in FIG. 4, and the redundant explanation may be omitted as appropriate.

The data processor 200b includes a corneal reflection image position identifying unit 260b, an alignment reference position identifying unit 230b, and an alignment target position calculator 240b.

The corneal reflection image position identifying unit 260b identifies the position of the corneal reflection image formed by projecting the light onto the subject's eye E by the projection optical system. For example, the corneal reflection image position identifying unit 260b identifies the corneal reflection image depicted in each of the pair of anterior segment images acquired by the anterior segment cameras 60A and 60B, and identifies the three-dimensional coordinate positions of the corneal reflection image positions using the same method as the three-dimensional position calculator 220.

The alignment reference position identifying unit 230b identifies the alignment reference position based on the corneal reflection image position identified by the corneal reflection image position identifying unit 260b. For example, the alignment reference position identifying unit 230b identifies the corneal apex position by subtracting the working distance from the Z position of the corneal reflection image position, using a known working distance uniquely determined by the optical system of the ophthalmic apparatus. The alignment reference position identifying unit 230b identifies the alignment reference position (Xr, Yr, Zr) from the X and Y positions of the corneal reflection image position and the corneal apex position (Z position).

The alignment target position calculator 240b calculates the alignment target position (Xr, Yr, Zr+Δs2) from the alignment reference position (Xr, Yr, Zr) identified by the alignment reference position identifying unit 230b. The alignment target position (Xr, Yr, Zr+Δs2) is a position shifted in the Z direction (working distance direction) by the shift amount Δs2 from the alignment reference position (Xr, Yr, Zr). Here, the shift amount Δs2 is a predetermined value that is uniquely defined by the optical arrangement of the optical systems in the ophthalmic apparatus. In the modification example of the second embodiment, the distance in the optical axis direction of the imaging optical system 40 from the identified corneal apex position to the imaging aperture conjugate position Pa is d, and a distance R1 from the corneal apex to the corneal reflection image position is replaced by R/2, and the alignment target position shifted by a component in the Z direction relative to the alignment reference position is calculated. Here, the shift amount Δs2 is determined so that (R1−d+Δs2) is equal to or greater than a predetermined gap threshold Gp.

The operation of the ophthalmic apparatus according to such present modification example is almost the same as that of the ophthalmic apparatus 1 according to the first embodiment. However, the present modification example differs from the first embodiment in that the corneal reflection image position is used for calculating the alignment target position.

Figure 14:
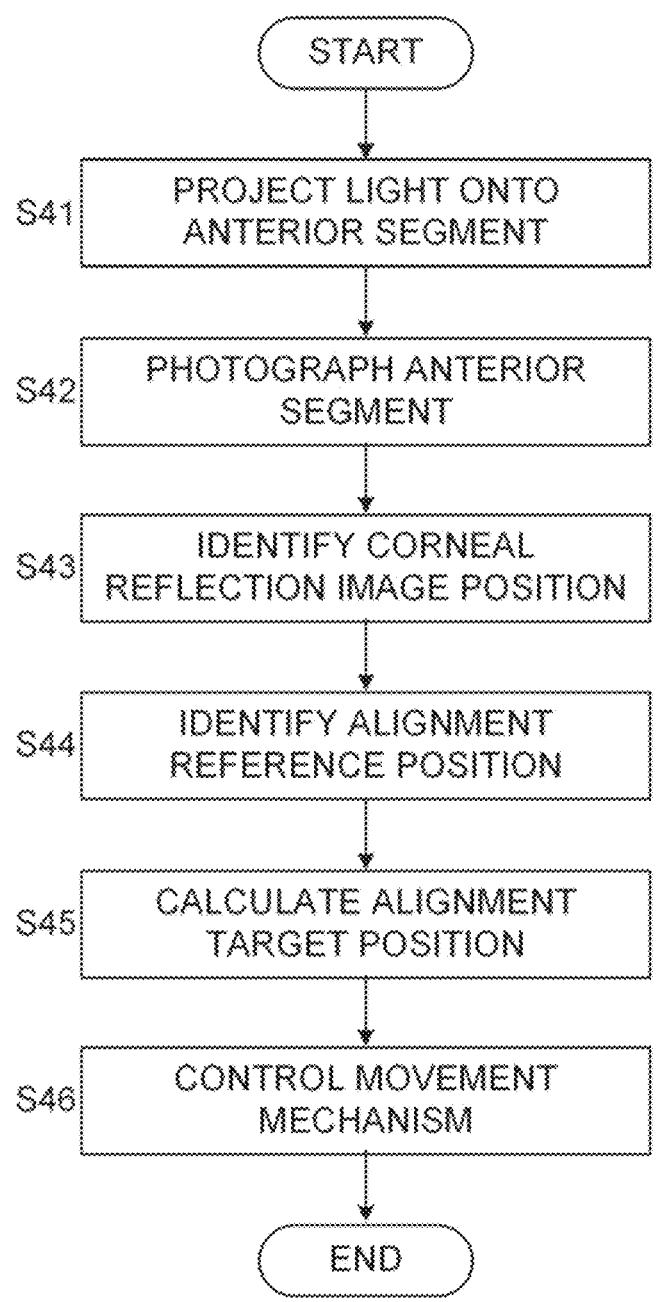
FIG. 14 is a flow chart of an example of an operation of the ophthalmic apparatus according to the modification example of the second embodiment.

In the present modification example, step S1 in FIG. 5 is performed according to the flow shown in FIG. 14.

FIG. 14 shows a flow chart of an example of the processing in step S1 in FIG. 5 according to the modification example of the second embodiment. The storage unit 102a stores computer program(s) for realizing the processing shown in FIG. 14. The main controller 101a operates according to the computer programs, and thereby the main controller 101a performs the processing shown in FIG. 14.

(S41: Project Light onto Anterior Segment)

First, the main controller 101a controls the projection optical system to project light onto the anterior segment Ea of the subject's eye E, as described above.

(S42: Photograph Anterior Segment)

Subsequently, the main controller 101a controls the anterior segment cameras 60A and 60B to start photographing the anterior segment Ea of the subject's eye E from different directions, and starts acquiring a pair of anterior segment images acquired substantially simultaneously.

(S43: Identify Corneal Reflection Image Position)

Next, the main controller 101a controls the corneal reflection image position identifying unit 260b to identify the corneal reflection image depicted in each of the pair of anterior segment images acquired in step S42, and identifies the three-dimensional coordinate positions of the corneal reflection image position using the same method as in step S13.

(S44: Identify Alignment Reference Position)

Next, the main controller 101a controls the alignment reference position identifying unit 230b to identify the alignment reference position based on the corneal reflection image position identified in step S43. Here, the alignment reference position identifying unit 230b identifies the alignment reference position (Xr, Yr, Zr), as described above.

(S45: Calculate Alignment Target Position)

Next, the main controller 101a controls the alignment target position calculator 240b to calculate the alignment target position (Xr, Yr, Zr+Δs2). The alignment target position (Xr, Yr, Zr+Δs2) is a position shifted in the Z direction (working distance direction) by the shift amount Δs2 from the alignment reference position (Xr, Yr, Zr) identified in step S44.

(S46: Control Movement Mechanism)

Next, the main controller 101a controls the movement mechanism 150 to arrange the subject's eye E at the alignment target position calculated in step S45.

This terminates the processing of step S1 in FIG. 5 in the modification example of the second embodiment (END).

According to such modification example of the second embodiment, the corneal reflection image position of the subject's eye E is identified, and the alignment target position is calculated with reference to the alignment reference position. Here, the alignment target position is a position shifted by the shift amount Δs2 in the optical axis direction of the imaging optical system 40, and the shift amount Δs2 is determined based on the identified corneal reflection image position. This makes it possible to control the movement mechanism 150 so that the light amount of the returning light passing through the imaging aperture 49 is reduced with greater precision than in the first embodiment.

As described above, according to the modification example of the second embodiment, it is possible to adjust the relative position of the optical system to the subject's eye more precisely than in the first embodiment so that the occurrence of flare can be suppressed without unnecessarily moving the optical system. As a result, the occurrence of flare included in the fundus images can be suppressed with high precision using a simple configuration, while suppressing the degradation of fundus image quality.

Third Embodiment

In the above embodiments, the cases have been described where, without extracting the occurrence of flare in the fundus image, the relative position of the optical system in the optical axis direction of the imaging optical system 40 to the subject's eye is changed so that the light amount of the returning light passing through the imaging aperture becomes less than when the distance in the optical axis direction between the imaging aperture conjugate position and the position of the corneal reflection image of the illumination light is (R/2−d) (or (R1−d)). However, the ophthalmic apparatus according to the embodiments is not limited to these. In a third embodiment, it is determined whether or not flare occurs, and when it is determined that the flare occurs, the relative position of the optical system in the optical axis direction of the imaging optical system 40 to the subject's eye is changed so that the light amount of the returning light passing through the imaging aperture becomes less than when the distance in the optical axis direction between the imaging aperture conjugate position and the position of the corneal reflection image of the illumination light is (R/2−d).

Hereinafter, a configuration and an operation of the ophthalmic apparatus according to the third embodiment will be described below mainly about the differences from the first embodiment.

The configuration of the optical system of the ophthalmic apparatus according to the third embodiment is the same configuration as that of the ophthalmic apparatus 1 according to the first embodiment. Further, the control system of the ophthalmic apparatus according to the third embodiment has a configuration in which a data processor 200c is provided instead of the data processor 200, in the configuration of the control system of the ophthalmic apparatus 1 according to the first embodiment.

Figure 15:
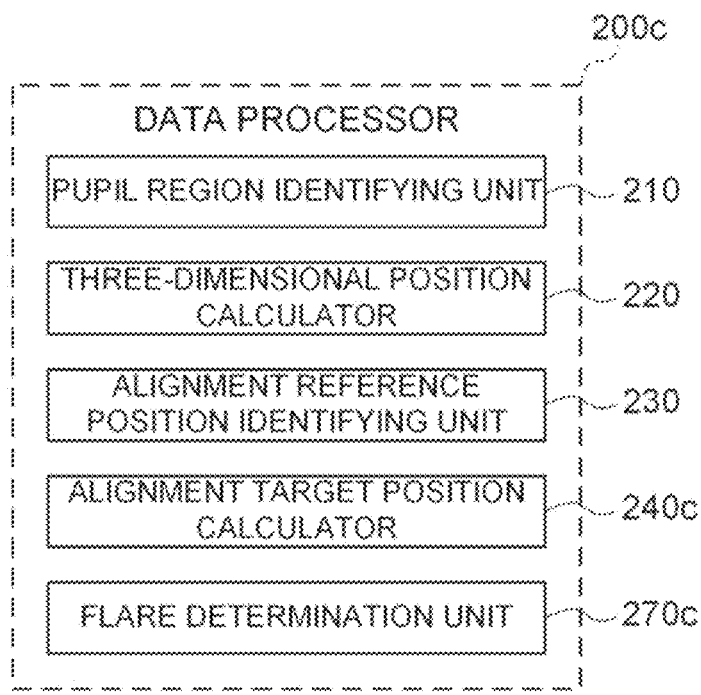
FIG. 15 is an example of a functional block diagram of an example of a configuration of the control system of an ophthalmic apparatus according to a third embodiment.

FIG. 15 shows a functional block diagram of an example of the configuration of the data processor 200c according to the third embodiments. In FIG. 15, like reference numerals designate like parts as in FIG. 4, and the redundant explanation may be omitted as appropriate.

The data processor 200c includes the pupil region identifying unit 210, the three-dimensional position calculator 220, the alignment reference position identifying unit 230, an alignment target position calculator 240c, and a flare determination unit 270c.

The flare determination unit 270c determines the state of flare in the fundus image. Examples of the state of flare include a presence or absence of flare. For example, the flare determination unit 270c determines that the flare occurs in the fundus image when the size (area) of an image region having a luminance value equal to or higher than a predetermined luminance value in the fundus image is equal to or greater than a first threshold value, and determines that the flare does not in the fundus image occur when the size is less than the first threshold value.

In some embodiments, the flare determination unit 270c determines the state of flare within a predetermined region in the fundus image. Examples of the predetermined region include a region including a characteristic site on the fundus Ef, and a region including a position corresponding to the optical axis of the imaging optical system 40.

In some embodiments, the flare determination unit 270c determines the state of flare based on the change in luminance in the region in the Y direction corresponding to the slit width on the fundus Ef from a luminance profile in a direction intersecting the X direction (slit direction) in the fundus image.

The alignment target position calculator 240c calculates the alignment target position based on the alignment reference position identified by the alignment reference position identifying unit 230. Specifically, the alignment target position calculator 240c calculates the alignment target position (Xr, Yr, Zr+Δs3) shifted by a predetermined shift amount Δs3 from the alignment reference position (Xr, Yr, Zr) in the Z direction (the working distance direction). Here, the shift amount Δs3 may be the shift amount Δs1 in the first embodiment. The shift amount Δs3 may be a shift amount (variable) corresponding to the size of the flare determined to be occurring by the flare determination unit 270c. Alternatively, the shift amount Δs3 may be a shift amount corresponding to the position in the fundus image of the flare determined to be occurring by the flare determination unit 270c.

The operation of the ophthalmic apparatus according to such third embodiment is almost the same as that of the ophthalmic apparatus 1 according to the first embodiment. However, the third embodiment differs from the first embodiment in that the alignment target position calculator 240c calculates the alignment target position when it is determined by the flare determination unit 270c that the flare occurs in the fundus image. In some embodiments, the calculation of the alignment target position, the control for the moving mechanism, and the determination of the state of flare are repeated until it is determined that the flare does not occur.

Figure 16:
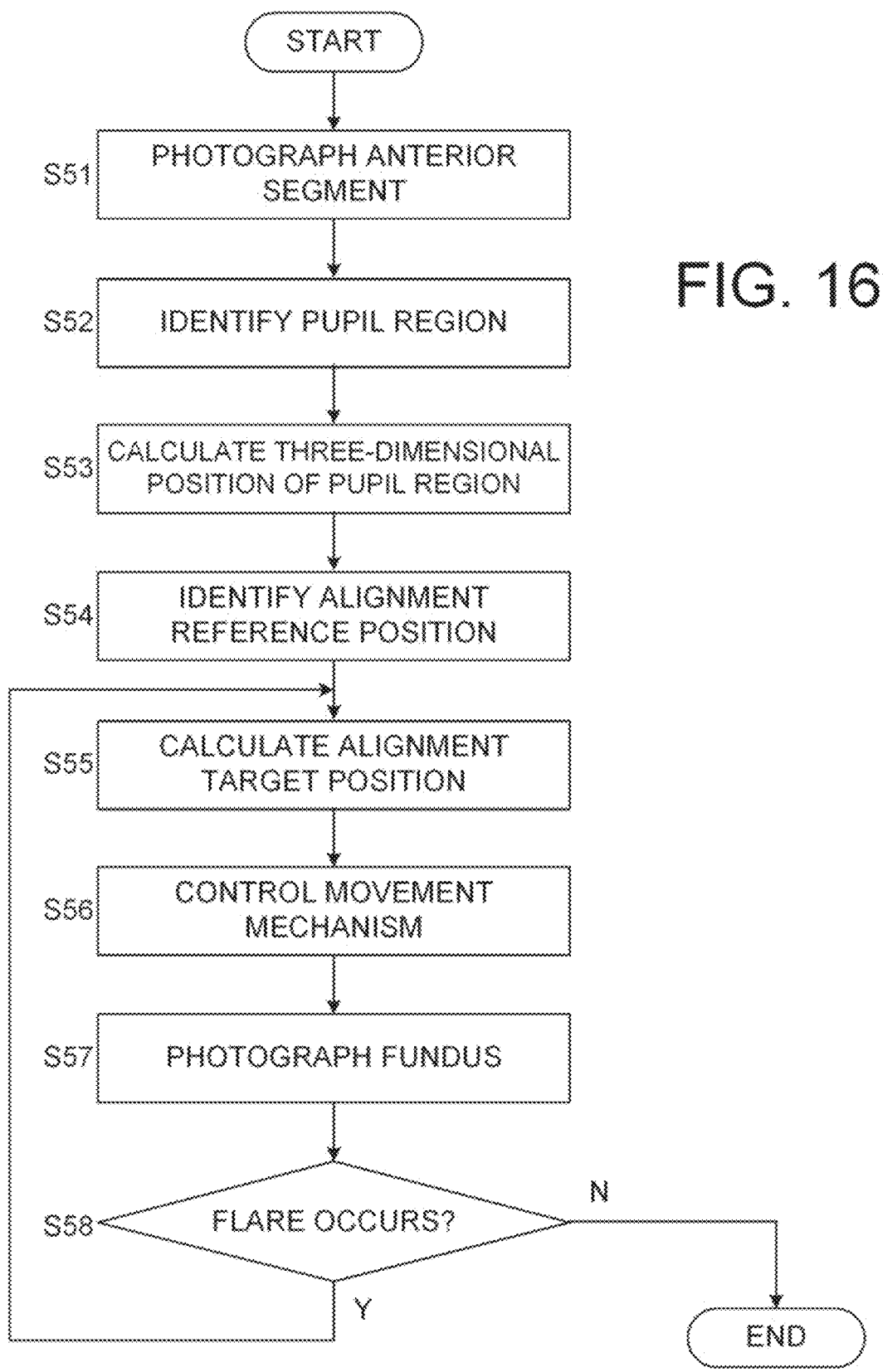
FIG. 16 is a flow chart of an example of an operation of the ophthalmic apparatus according to the third embodiment.

In the third embodiment, the processing in step S1 in FIG. 5 is performed according to the flow shown in FIG. 16.

FIG. 16 shows a flow chart of an example of the processing in step S1 in FIG. 5 according to the third embodiment. The storage unit 102 stores computer program(s) for realizing the processing shown in FIG. 16. The main controller 101 operates according to the computer programs, and thereby the main controller 101 performs the processing shown in FIG. 16.

(S51: Photograph Anterior Segment)

First, similar to step S11, the main controller 101 controls the anterior segment cameras 60A and 60B to start photographing the anterior segment Ea of the subject's eye E from different directions, and starts acquiring a pair of anterior segment images acquired substantially simultaneously.

(S52: Identify Pupil Region)

Next, similar to step S12, the main controller 101 controls the pupil region identifying unit 210 to identify the pupil region for each of the pair of anterior segment images acquired in step S51.

(S53: Calculate Three-Dimensional Position of Pupil Region)

Next, similar to step S13, the main controller 101 controls the three-dimensional position calculator 220 to calculate the three-dimensional position of the pupil region using the pair of anterior eye images identified in step S52, as described above.

(S54: Identify Alignment Reference Position)

Subsequently, similar to step S14, the main controller 101 controls the alignment reference position identifying unit 230 to identify the corneal apex position as the alignment reference position from the three-dimensional position of the pupil region calculated in step S53.

(S55: Calculate Alignment Target Position)

Subsequently, the main controller 101 controls the alignment target position calculator 240c to calculate the alignment target position shifted by a predetermined shift amount Δs3 in the optical axis direction of the imaging optical system 40 with reference to the alignment reference position identified in step S54.

(S56: Control Movement Mechanism)

Next, the main controller 101 controls the movement mechanism 150 to arrange the subject's eye E at the alignment target position calculated in step S55.

(S57: Photograph Fundus)

Subsequently, the main controller 101 controls the illumination optical system 20, the optical scanner 30, the imaging optical system 40, and the imaging device 50, in a state where the optical system has been moved in step S56, to photograph the fundus Ef of the subject's eye E, and acquires the fundus image.

(S58: Flare Occurs?)

Next, the main controller 101 controls the flare determination unit 270c to determine whether or not the flare occurs in the fundus image acquired in step S57. When it is determination that the flare occurs in the fundus image (S58: Y), the processing of the of step S1 in FIG. 5 proceeds to step S55. When it is determined that the flare does not occur in the fundus image (S58: N), the processing of step S1 in FIG. 5 is terminated (END).

According to such third embodiment, the alignment target position shifted in the optical axis direction of the imaging optical system 40 by the predetermined shift amount Δs3 with reference to the alignment reference position is calculated, while checking the occurrence of flare. This makes it possible to control the movement mechanism 150 so that the light amount of the returning light passing through the imaging aperture 49 is reduced, as in the first embodiment.

In the third embodiment, without determining the state of flare in the fundus image, the user may perform operation on the operation unit 110 while viewing the fundus image, and the main controller 101 may control the movement mechanism 150 based on the operation content for the operation unit. This also enables the occurrence of flare to be suppressed manually.

It should be noted that the third embodiment can be applied to the first embodiment, the second embodiment, or the modification example of the second embodiment.

As described above, according to the third embodiment, it is possible to adjust the relative position of the optical system to the subject's eye with high precision so as to suppress the occurrence of flare, while checking the occurrence of flare. As a result, the occurrence of flare included in the fundus images can be suppressed with high precision using a simple configuration, while suppressing the degradation of fundus image quality.

Fourth Embodiment

In the above embodiments or the modification example thereof, the cases have been described where the light amount passing through the imaging aperture 49 is reduced by arranging the subject's eye E at the alignment target position shifted from the alignment reference position. However, the configuration of the ophthalmic apparatus according to the embodiments is not limited thereto. In a fourth embodiment, the subject's eye E is placed at the alignment reference position and the imaging aperture 49 is moved in the optical axis direction to reduce the light amount passing through the imaging aperture 49.

Hereinafter, the configuration and the operation of the ophthalmic apparatus according to the fourth embodiment will be described, focusing on the differences from the ophthalmic apparatus 1 according to the first embodiment.

Figure 17:
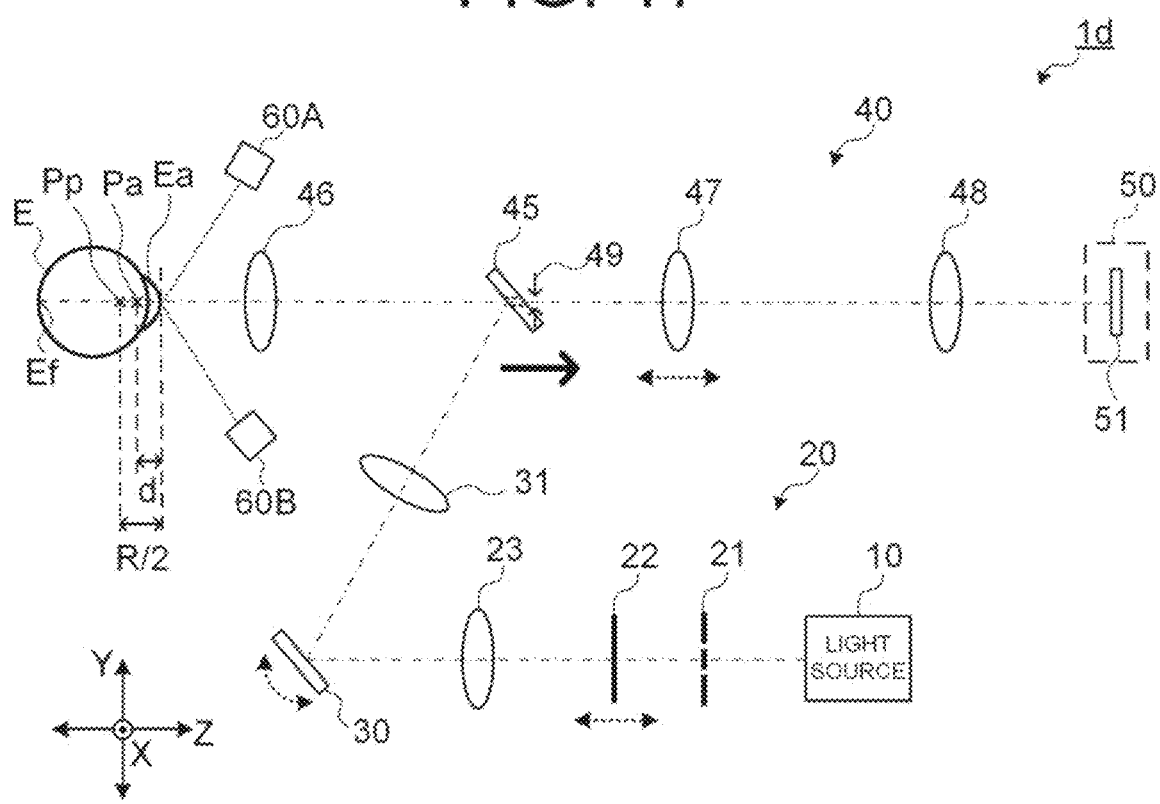
FIG. 17 is a schematic diagram illustrating an example of a configuration of an optical system of an ophthalmic apparatus according to a fourth embodiment.

FIG. 17 shows an example of the configuration of the optical system of the ophthalmic apparatus 1d according to the fourth embodiment. In FIG. 17, like reference numerals designate like parts as in FIG. 1, and the redundant explanation may be omitted as appropriate.

The difference between the configuration of the optical system of the ophthalmic apparatus 1d and that of the ophthalmic apparatus 1 according to the first embodiment is that the imaging aperture 49 is movable in the optical axis direction of the imaging optical system 40. In other words, the imaging aperture 49 is moved by a movement amount corresponding to the shift amount of the optical system in the optical axis direction of the imaging optical system 40 with reference to the alignment reference position in the above embodiments or the modification example thereof.

Figure 18:
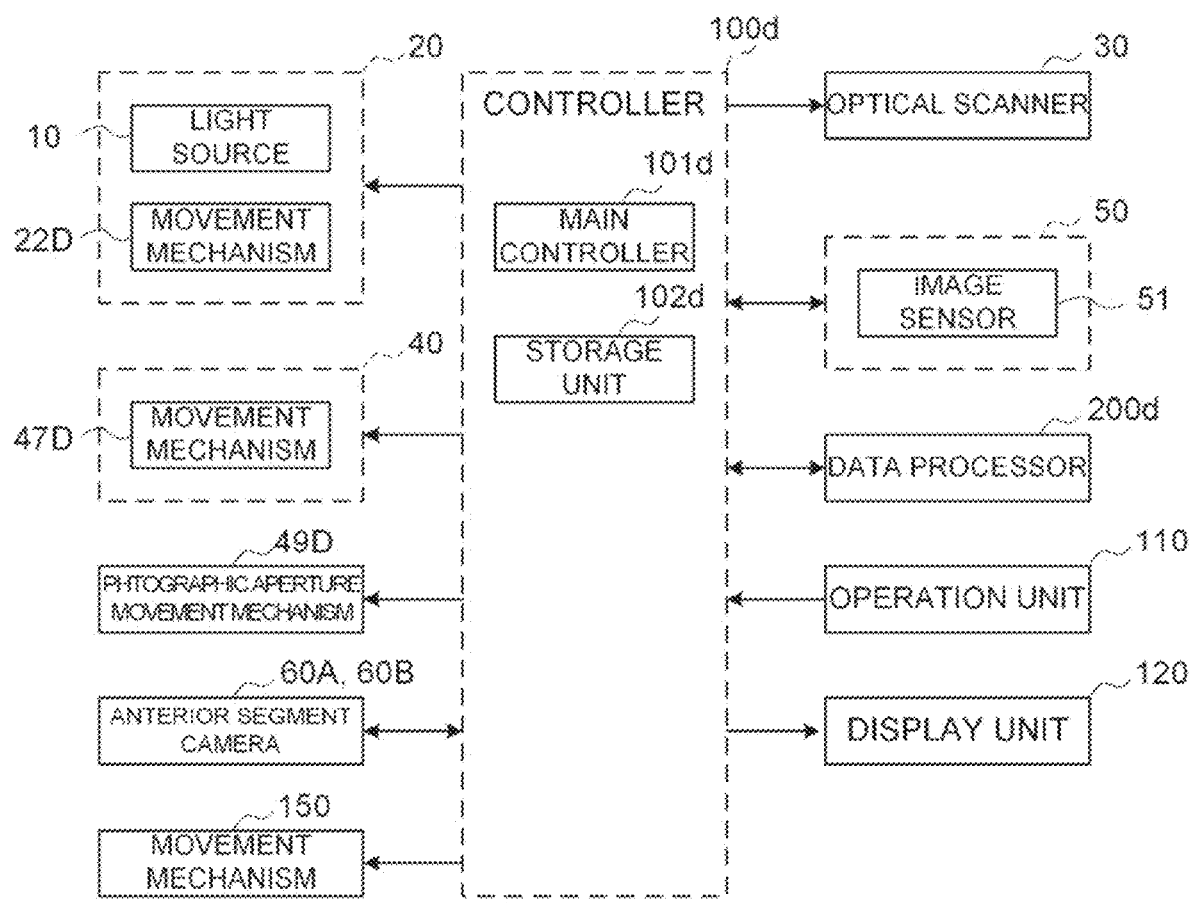
FIG. 18 is a schematic diagram illustrating an example of a configuration of a control system of the ophthalmic apparatus according to the fourth embodiment.

FIG. 18 shows a functional block diagram of an example of the configuration of a control system of the ophthalmic apparatus 1d according to the fourth embodiment. In FIG. 18, like reference numerals designate like parts as in FIG. 3, and the redundant explanation may be omitted as appropriate.

The differences between the configuration of the control system of the ophthalmic apparatus 1d and that of the ophthalmic apparatus 1 according to the first embodiment are that a controller 100d is provided instead of the controller 100, that an imaging aperture movement mechanism 49D that moves the imaging aperture 49 is added, and that a data processor 200d is provided instead of the data processor 200.

The controller 100d includes a main controller 101d and a storage unit 102d.

In addition to the control performed by the main controller 101, the main controller 101*d* can perform control for the imaging aperture movement mechanism 49D and control for the data processor 200*d*.

Assuming that the lateral magnification from the pupil (near the pupil) of the subject's eye E to the imaging aperture 49 is a known Q times, the longitudinal magnification is $Q^2$ times. Therefore, the main controller 101*d* shifts the imaging aperture 49 in the direction away from the subject's eye E by an shift amount ($\Delta s \times Q^2$) in the optical axis direction of the imaging optical system 40. Here, $\Delta s$ is a predetermined shift amount, as in the first embodiment.

The storage unit 102*d* stores the same information as the storage unit 102, and also stores program(s) executed by the main controller 101*d*.

The imaging aperture movement mechanism 49D includes an actuator, and moves the imaging aperture 49 in the optical axis direction of the imaging optical system 40, under the control from the main controller 101*d*.

Figure 19:
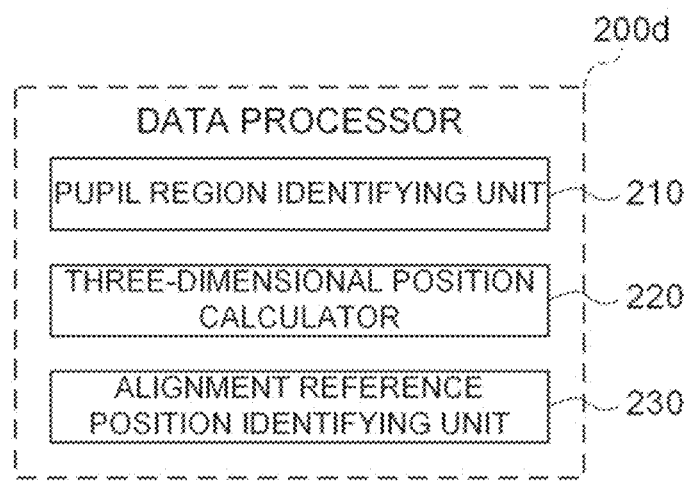
FIG. 19 is a schematic diagram illustrating an example of a configuration of a control system of the ophthalmic apparatus according to the fourth embodiment.

FIG. 19 shows a functional block diagram of an example of the configuration of the data processor 200*d* according to the fourth embodiment. In FIG. 19, like reference numerals designate like parts as in FIG. 4, and the redundant explanation may be omitted as appropriate.

The data processor 200*d* includes the pupil region identifying unit 210, the three-dimensional position calculator 220, and the alignment reference position identifying unit 230.

The operation of the ophthalmic apparatus according to such fourth embodiment is almost the same as that of the ophthalmic apparatus 1 according to the first embodiment. However, the fourth embodiment differs from the first embodiment in that the main controller 101*d* controls the movement mechanism 150 to arrange the subject's eye E at the alignment reference position and controls the imaging aperture movement mechanism 49D to reduce the light amount of the returning light of the illumination passing through the imaging aperture 49.

Figure 20:
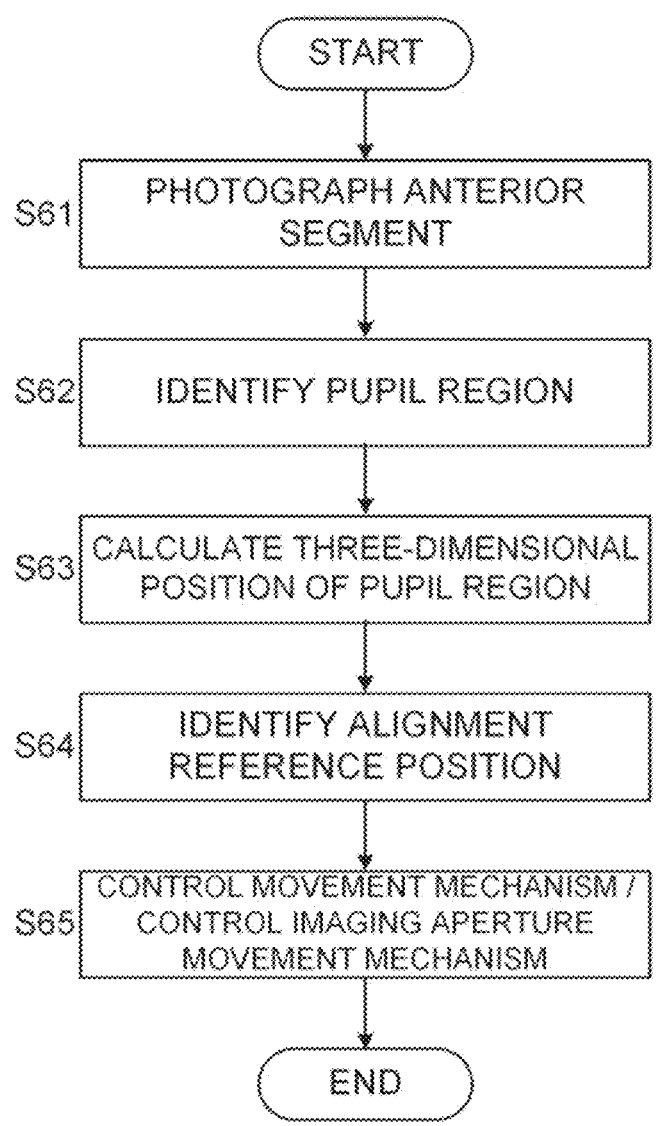
FIG. 20 is a flow chart of an example of an operation of the ophthalmic apparatus according to the fourth embodiment.

In the fourth embodiment, the processing in step S1 in FIG. 5 is performed according to the flow shown in FIG. 20.

FIG. 20 shows a flow chart of an example of the processing in step S1 in FIG. 5 according to the fourth embodiment. The storage unit 102*d* stores computer program(s) for realizing the processing shown in FIG. 20. The main controller 101*d* operates according to the computer programs, and thereby the main controller 101*d* performs the processing shown in FIG. 20.

(S61: Project Light onto Anterior Segment)

First, similar to step S11, the main controller 101*d* controls the projection optical system to project light onto the anterior segment Ea of the subject's eye E.

(S62: Photograph anterior segment)

Subsequently, similar to step S12, the main controller 101*d* controls the anterior segment cameras 60A and 60B to start photographing the anterior segment Ea of the subject's eye E from different directions, and starts acquiring a pair of anterior segment images acquired substantially simultaneously.

(S63: Calculate Three-Dimensional Position of Pupil Region)

Next, similar to step S13, the main controller 101*d* controls the three-dimensional position calculator 220 to calculate the three-dimensional position of the pupil region using the pair of anterior eye images identified in step S62.

(S64: Identify Alignment Reference Position)

Subsequently, similar to step S14, the main controller 101*d* controls the alignment reference position identifying unit 230 to identify the corneal apex position as the alignment reference position from the three-dimensional position of the pupil region calculated in step S63.

(S65: Control Movement Mechanism/Control Imaging Aperture Movement Mechanism)

Next, the main controller 101*d* controls the movement mechanism 150 to arrange the subject's eye E at the alignment reference position identified in step S64, and controls the imaging aperture movement mechanism 49D to move the imaging aperture 49 in the optical axis direction of the imaging optical system 40 by the shift amount ($\Delta s \times Q^2$).

This terminates the processing of step S1 in FIG. 5 in the fourth embodiment (END).

According to such fourth embodiment, without controlling the movement mechanism 150 so as to arrange the subject's eye E at the alignment target position shifted from the alignment reference position, the imaging aperture 49 can be moved.

As described above, according to the fourth embodiment, it is possible to adjust the relative position of the optical system to the subject's eye with high precision so as to suppress the occurrence of flare without unnecessarily moving the optical system. As a result, the occurrence of flare included in the fundus images can be suppressed with high precision using a simple configuration, while suppressing the degradation of fundus image quality.

Fifth Embodiment

In the fourth embodiment, the in the same way as the second embodiment, the corneal apex position of the subject's eye E may be measured, and the alignment target position may be calculated using the corneal apex position, which is obtained by measurement, and the corneal curvature radius.

Hereinafter, the ophthalmic apparatus according to a fifth embodiment will be described below mainly about the differences from the fourth embodiment.

The configuration of the optical system of the ophthalmic apparatus according to the fifth embodiment has a configuration in which the corneal apex detection optical system 70 shown in FIG. 9 is added to the configuration of the optical system of the ophthalmic apparatus 1*d* according to the fourth embodiment. Further, the configuration of the control system of the ophthalmic apparatus according to the fifth embodiment has a configuration in which the corneal apex position identifying unit 250*a* is added to the configuration of the data processor shown in FIG. 19.

The operation of the ophthalmic apparatus according to such fifth embodiment is almost the same as that of the ophthalmic apparatus 1*d* according to the fourth embodiment. However, the fifth embodiment differs from the fourth embodiment in that the corneal apex position detected using the corneal apex detection optical system 70 is used for calculating the alignment target position, and that the main controller 101*d* moves the imaging aperture 49 in the direction away from the subject's eye E by the shift amount ($\Delta s1 \times Q^2$) in the optical axis direction of the imaging optical system 40. Here, $\Delta s1$ is a predetermined shift amount, as in the second embodiment.

Figure 21:
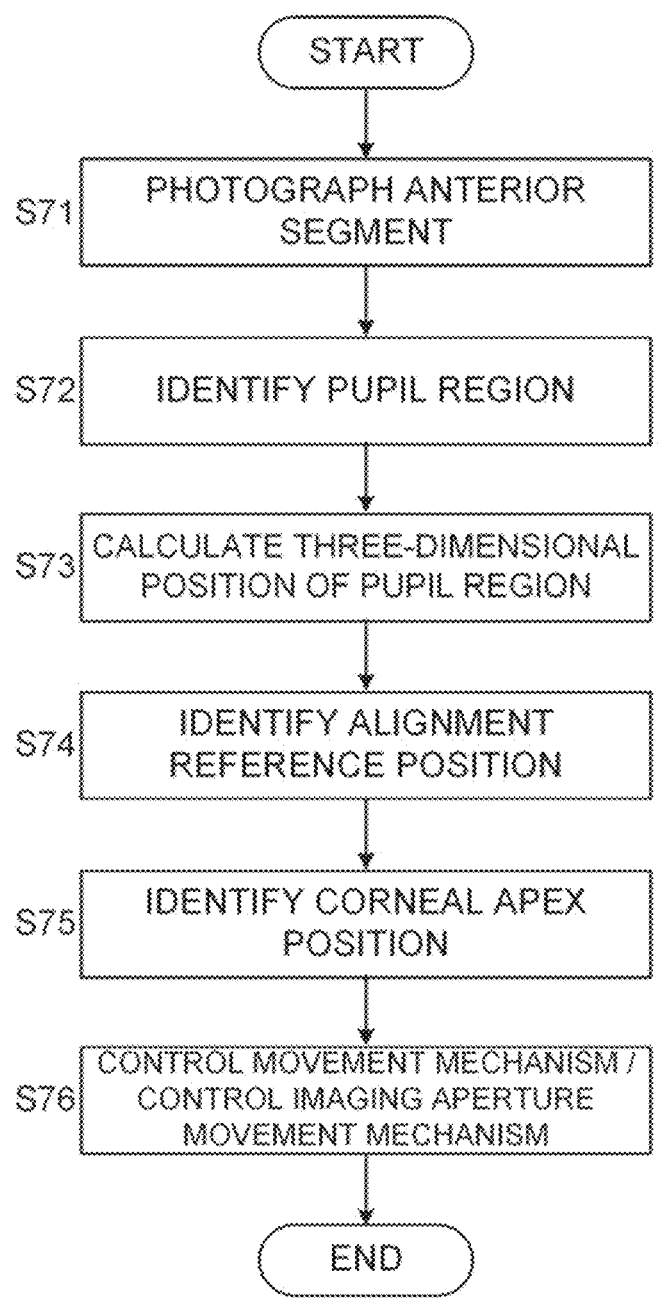
FIG. 21 is a flow chart of an example of an operation of an ophthalmic apparatus according to a fifth embodiment.

In the fifth embodiment, the processing in step S1 in FIG. 5 is performed according to the flow shown in FIG. 21.

FIG. 21 shows a flow chart of an example of the processing in step S1 in FIG. 5 according to the fifth embodiment. The storage unit 102*d* stores computer program(s) for realizing the processing shown in FIG. 21. The main controller 101d operates according to the computer programs, and thereby the main controller 101d performs the processing shown in FIG. 21.

(S71: Photograph Anterior Segment)

First, similar to step S61, the main controller 101d controls the anterior segment cameras 60A and 60B to start photographing the anterior segment Ea of the subject's eye E from different directions, and starts acquiring a pair of anterior segment images acquired substantially simultaneously.

(S72: Identify Pupil Region)

Next, similar to step S62, the main controller 101d controls the pupil region identifying unit 210 to identify the position of pupil region for each of the pair of the anterior segment images acquired in step S71.

(S73: Calculate Three-Dimensional Position of Pupil Region)

Next, similar to step S63, the main controller 101d controls the three-dimensional position calculator 220 to calculate the three-dimensional position of the pupil region using the pair of anterior eye images identified in step S72.

(S74: Identify Alignment Reference Position)

Subsequently, similar to step S64, the main controller 101d controls the alignment reference position identifying unit 230 to identify the alignment reference corneal apex position by position from the three-dimensional position of the pupil region calculated in step S73.

(S75: Identify Corneal Apex Position)

Subsequently, similar to step S5, the main controller 101d causes the light from the light source 71 to irradiate the anterior segment of the subject's eye E using the corneal apex detection optical system 70, and to obtain the received position of the reflected light on the light receiving surface of the line sensor 72. The main controller 101d controls the corneal apex position identifying unit 250a to identify the corneal apex position of the subject's eye E from the obtained received position of the reflected light on the light receiving surface of the line sensor 72. For example, the Z position of the alignment reference position identified in step S74 is replaced with the corneal apex position identified in step S75.

(S76: Control Movement Mechanism)

Next, similar to step S65, the main controller 101d controls the movement mechanism 150 to arrange the subject's eye E at the alignment reference position identified in steps S74 and S75, and controls the imaging aperture movement mechanism 49D to move the imaging aperture 49 in the optical axis direction of the imaging optical system 40 by the shift amount ($\Delta s1 \times Q^2$).

This terminates the processing of step S1 in FIG. 5 in the fifth embodiment (END).

According to such fifth embodiment, the subject's eye E is arranged at the alignment reference position including the corneal apex position of the subject's eye E identified using the corneal apex detection optical system 70, and the imaging aperture 49 is moved by $\Delta s1$ in the optical axis direction of the imaging optical system 40. Here, $\Delta s1$ is determined based on the corneal apex position and the corneal curvature radius. This makes it possible to control the movement mechanism 150 so that the light amount of the returning light passing through the imaging aperture 49 is reduced with greater precision than in the fourth embodiment.

As described above, according to the fifth embodiment, it is possible to adjust the relative position of the optical system to the subject's eye more precisely than in the first embodiment so that the occurrence of flare can be suppressed without unnecessarily moving the optical system. As a result, the occurrence of flare included in the fundus images can be suppressed with high precision using a simple configuration, while suppressing the degradation of fundus image quality.

Modification Example of Fifth Embodiment

In the fifth embodiment, the case has been described where the corneal apex position of the subject's eye E is detected, and the alignment reference position is calculated using the detected corneal apex position and the corneal curvature radius. However, the configuration according to the embodiments is not limited to this. In a modification example of the fifth embodiment, similar to the modification example of the second embodiment, the corneal reflection image position (Purkinje image position) of the illumination light is detected, and the alignment reference position is calculated using the detected corneal reflection image.

Hereinafter, the configuration of the ophthalmic apparatus according to the modification example of the fifth embodiment will be described mainly about the differences from the fourth embodiment.

The optical system of the ophthalmic apparatus according to the modification example of the fifth embodiment has a configuration in which a projection optical system (not shown) that projects light onto the subject's eye is added to the configuration of the optical system of the ophthalmic apparatus 1d according to the fourth embodiment. The control system of the ophthalmic apparatus according to the present modification example has a configuration in which the corneal reflection image position identifying unit 260b is added in the data processor 200d, in the configuration of the control system of the ophthalmic apparatus 1d according to the fourth embodiment.

The operation of the ophthalmic apparatus according to the modification example of the fifth embodiment is the same as that of the ophthalmic apparatus 1d according to the fourth embodiment. However, the modification example of the fifth embodiment differs from the fourth embodiment in that the corneal reflection image position is used for calculating the alignment target position, and that the main controller 101d moves the imaging aperture 49 in the direction away from the subject's eye E by the shift amount ($\Delta s2 \times Q^2$) in the optical axis direction of the imaging optical system 40. Here, $\Delta s2$ is a predetermined shift amount, as in the modification example of the second embodiment.

Figure 22:
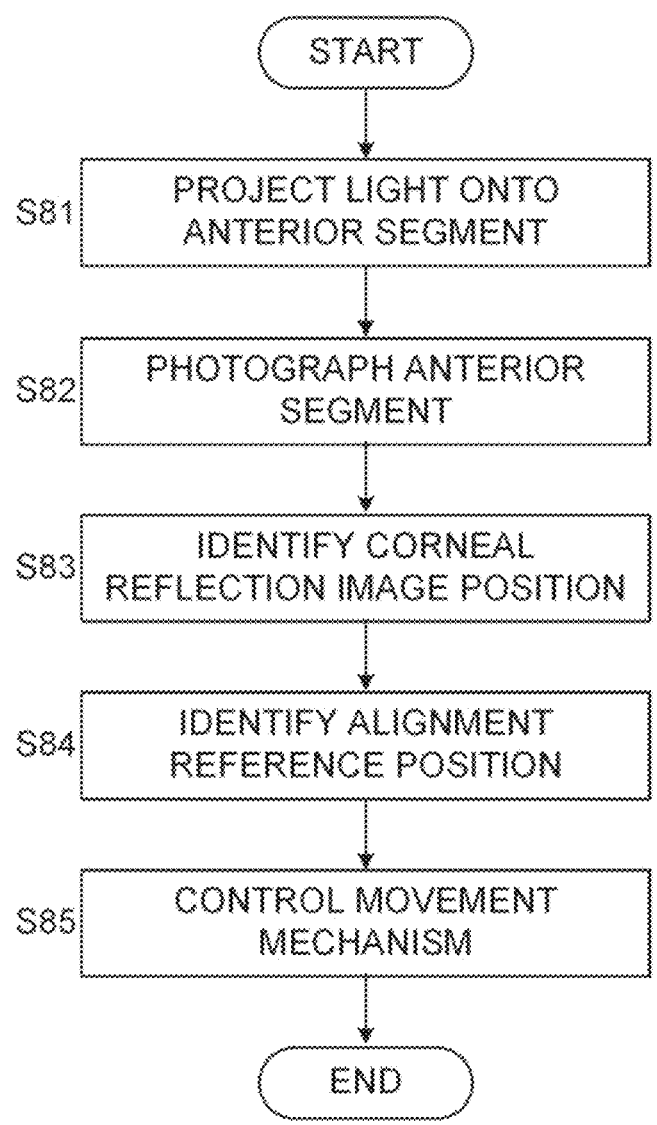
FIG. 22 is a flow chart of an example of an operation of an ophthalmic apparatus according to a modification example of the fifth embodiment.

In the present modification example, step S1 in FIG. 5 is performed according to the flow shown in FIG. 22.

FIG. 22 shows a flow chart of an example of the processing in step S1 in FIG. 5 according to the modification example of the fifth embodiment. The storage unit 102d stores computer program(s) for realizing the processing shown in FIG. 22. The main controller 101d operates according to the computer programs, and thereby the main controller 101d performs the processing shown in FIG. 22.

(S81: Project Light onto Anterior Segment)

First, similar to step S41, the main controller 101d controls the projection optical system to project light onto the anterior segment Ea of the subject's eye E.

(S82: Photograph Anterior Segment)

Subsequently, similar to step S42, the main controller 101d controls the anterior segment cameras 60A and 60B to start photographing the anterior segment Ea of the subject's eye E from different directions, and starts acquiring a pair of anterior segment images acquired substantially simultaneously.

(S83: Identify Corneal Reflection Image Position)

Next, similar to step S43, the main controller 101d controls the corneal reflection image position identifying unit 260b to identify the corneal reflection image depicted in each of the pair of anterior segment images acquired in step S82, and identifies the three-dimensional coordinate positions of the corneal reflection image position using the same method as in step S13.

(S84: Identify Alignment Reference Position)

Next, similar to step S44, the main controller 101d controls the alignment reference position identifying unit 230 to identify the alignment reference position based on the corneal reflection image position identified in step S83.

(S85: Control Movement Mechanism)

Next, similar to step S65, the main controller 101d controls the movement mechanism 150 to arrange the subject's eye E at the alignment reference position identified in step S84, and controls the imaging aperture movement mechanism 49D to move the imaging aperture 49 in the optical axis direction of the imaging optical system 40 by the shift amount ($\Delta s2 \times Q^2$).

This terminates the processing of step S1 in FIG. 5 in the modification example of the fifth embodiment (END).

According to the modification example of the fifth embodiment, the subject's eye E is arranged at the alignment reference position including the corneal reflection image position of the subject's eye E. and the imaging aperture 49 is moved by the shift amount determined based on the corneal reflection image position in the optical axis direction of the imaging optical system 40. This makes it possible to control the movement mechanism 150 so that the light amount of the returning light passing through the imaging aperture 49 is reduced with greater precision than in the fourth embodiment.

As described above, according to the modification example of the fifth embodiment, it is possible to adjust the relative position of the optical system to the subject's eye more precisely than in the first embodiment so that the occurrence of flare can be suppressed without unnecessarily moving the optical system. As a result, the occurrence of flare included in the fundus images can be suppressed with high precision using a simple configuration, while suppressing the degradation of fundus image quality.

Sixth Embodiment

In the fourth embodiment, the fifth embodiment, and the modification examples of thereof, the cases have been described where, without extracting the occurrence of flare in the fundus image, the position of the imaging aperture 49 in the optical axis direction of the imaging optical system 40 is changed so that the light amount of the returning light passing through the imaging aperture becomes less than when the distance in the optical axis direction of the imaging optical system between the imaging aperture conjugate position and the position of the corneal reflection image of the illumination light is (R/2−d) (or (R1−d)). However, the ophthalmic apparatus according to the embodiments is not limited to these. In a sixth embodiment, it is determined whether or not flare occurs, and when it is determined that the flare occurs, the position of the imaging aperture 49 in the optical axis direction of the imaging optical system 40 is changed so that the light amount of the returning light passing through the imaging aperture becomes less than when the distance in the optical axis direction between the imaging aperture conjugate position and the position of the corneal reflection image of the illumination light is (R/2−d).

Hereinafter, the configuration and the operation of the ophthalmic apparatus according to the sixth embodiment will be described below mainly about the differences from the fourth embodiment.

The configuration of the optical system of the ophthalmic apparatus according to the sixth embodiment is the same configuration as that of the ophthalmic apparatus 1d according to the fourth embodiment. Further, the control system of the ophthalmic apparatus according to the sixth embodiment has a configuration in which the flare determination unit 270c according to the third embodiment is added to the configuration of the control system of the ophthalmic apparatus 1d according to the fourth embodiment in the data processor 200.

The operation of the ophthalmic apparatus according to such sixth embodiment is almost the same as that of the ophthalmic apparatus 1 according to the first embodiment. However, the sixth embodiment differs from the fourth embodiment in that the alignment target position calculator 240c calculates the alignment target position when it is determined by the flare determination unit 270c that the flare occurs in the fundus image, and that the main controller 101d moves the imaging aperture 49 in the direction away from the subject's eye E by a shift amount ($\Delta s3 \times Q^2$) in the optical axis direction of the imaging optical system 40. Here, $\Delta s3$ is a predetermined shift amount, as in the modification example of the third embodiment. In some embodiments, the calculation of the alignment target position, the control for the moving mechanism, and the determination of the state of flare are repeated until it is determined that the flare does not occur.

Figure 23:
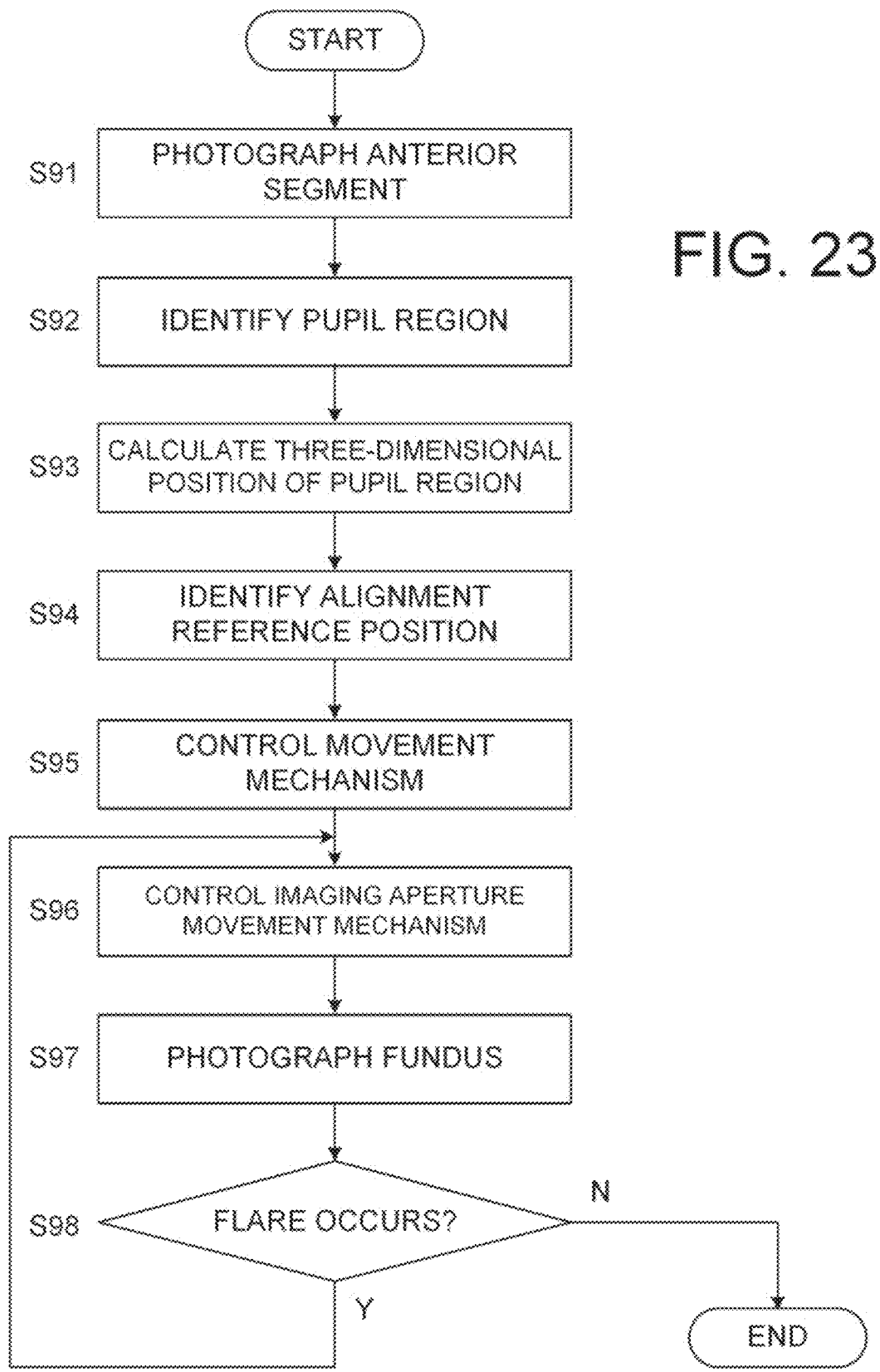
FIG. 23 is a flow chart of an example of an operation of an ophthalmic apparatus according to a sixth embodiment.

In the sixth embodiment, the processing in step S1 in FIG. 5 is performed according to the flow shown in FIG. 23.

FIG. 23 shows a flow chart of an example of the processing in step S1 in FIG. 5 according to the sixth embodiment. The storage unit 102d stores computer program(s) for realizing the processing shown in FIG. 23. The main controller 101d operates according to the computer programs, and thereby the main controller 101d performs the processing shown in FIG. 23.

(S91: Photograph Anterior Segment)

First, similar to step S61, the main controller 101d controls the anterior segment cameras 60A and 60B to start photographing the anterior segment Ea of the subject's eye E from different directions, and starts acquiring a pair of anterior segment images acquired substantially simultaneously.

(S92: Identify Pupil Region)

Next, similar to step S62, the main controller 101d controls the pupil region identifying unit 210 to identify the position of pupil region for each of the pair of the anterior segment images acquired in step S91.

(S93: Calculate Three-Dimensional Position of Pupil Region)

Next, similar to step S63, the main controller 101d controls the three-dimensional position calculator 220 to calculate the three-dimensional position of the pupil region using the pair of anterior eye images identified in step S92, as described above.

(S94: Identify Alignment Reference Position)

Subsequently, similar to step S64, the main controller 101d controls the alignment reference position identifying unit 230 to identify the corneal apex position as the alignment reference position from the three-dimensional position of the pupil region calculated in step S93.

(S95: Control Movement Mechanism)

Next, the main controller 101d controls the movement mechanism 150 to arrange the subject's eye E at the alignment reference position calculated in step S94.

(S96: Control Imaging Aperture Movement Mechanism)

Subsequently, the main controller 101d controls the imaging aperture movement mechanism 49D to move the imaging aperture 49 in the optical axis direction of the imaging optical system 40 by the shift amount ($\Delta s3 \times Q^2$).

(S97: Photograph Fundus)

Subsequently, similar to step S57, the main controller 101d controls the illumination optical system 20, the optical scanner 30, the imaging optical system 40, and the imaging device 50, in a state where the optical system has been moved in steps S95 and S96, to photograph the fundus Ef of the subject's eye E, and acquires the fundus image.

(S98: Flare Occurs?)

Next, similar to step S58, the main controller 101d controls the flare determination unit 270c to determine whether or not the flare occurs in the fundus image acquired in step S97. When it is determination that the flare occurs in the fundus image (S98: Y), the processing of the of step S1 in FIG. 5 proceeds to step S96. When it is determined that the flare does not occur in the fundus image (S98: N), the processing of step S1 in FIG. 5 is terminated (END).

The movement amount of the imaging aperture 49 in the optical axis direction of the imaging optical system 40 in step S96 when proceeding from step S98 to step S96 may be the same or different from the previous movement amount. In some embodiments, the movement amount of the imaging aperture 49 in the optical axis direction of the imaging optical system 40 in step S96 when proceeding from step S98 to step S96 is changed in accordance with the state of flare detected in step S98. For example, depending on the size of the flare determined by the flare determination unit 270c, the movement amount after the second and subsequent of the imaging aperture 49 is changed.

According to such sixth embodiment, while checking the occurrence of flare, the optical system is moved with reference to the alignment reference position, and the alignment target position where the imaging aperture 49 is shifted in the optical axis direction of the imaging optical system 40 is calculated. This makes it possible to control the imaging aperture movement mechanism 49d so that the light amount of the returning light passing through the imaging aperture 49 is reduced, as in the fourth embodiment.

In the sixth embodiment, without determining the state of flare in the fundus image, the user may perform operation on the operation unit 110 while viewing the fundus image, and the main controller 101d may control the imaging aperture movement mechanism 49D based on the operation content for the operation unit. This also enables the occurrence of flare to be suppressed manually.

It should be noted that the sixth embodiment can be applied to the fourth embodiment, the fifth embodiment, or the modification example of the fifth embodiment.

As described above, according to the sixth embodiment, it is possible to adjust the relative position of the optical system to the subject's eye with high precision so as to suppress the occurrence of flare, while checking the occurrence of flare. As a result, the occurrence of flare included in the fundus images can be suppressed with high precision using a simple configuration, while suppressing the degradation of fundus image quality.

In the fourth embodiment, the fifth embodiment, the modification example of the fifth embodiment, or the sixth embodiment, without moving the imaging aperture 49 in the optical axis direction, a size of an aperture formed in the imaging aperture 49 may be configured to be changeable. By changing the size of the aperture formed in the imaging aperture 49, the light amount of the returning light of the illumination light that passes through the imaging aperture 49 and is guided to the image sensor 51 can be reduced.

[Actions]

The ophthalmic apparatus, the method of controlling the ophthalmic apparatus, and the program according to the embodiments will be explained.

The first aspect of some embodiments is an ophthalmic apparatus (1, 1a, 1d) including an optical system (light source 10, illumination optical system 20, optical scanner 30, imaging optical system 40, and imaging device 50), a movement mechanism (150), a controller (100, 100a, 100d, main controller 101, 101a, 101d). The optical system includes an illumination optical system (20) and an imaging optical system (40). The illumination optical system is configured to illuminate a fundus (Ef) of a subject's eye (E) with illumination light, the imaging optical system having an imaging aperture (49) and being configured to guide returning light from the subject's eye having passed through the imaging aperture to an imaging sensor (51). The movement mechanism is configured to relatively move the subject's eye and the optical system in an optical axis direction of the imaging optical system. The controller is configured to control the movement mechanism. When a corneal curvature radius is R and a distance from a corneal apex position to an imaging aperture conjugate position substantially conjugate optically to the imaging aperture is d, the controller is configured to control the movement mechanism so that light amount of the returning light passing through the imaging aperture becomes less than when a distance in the optical axis direction between the imaging aperture conjugate position and a position of a corneal reflection image of the illumination light is (R/2−d).

According to such an aspect, the relative position of the optical system to the subject's eye is changed so that the light amount of the returning light passing through the imaging aperture is less than when the distance in the optical axis direction of the imaging optical system between the imaging aperture conjugate position and the position of the corneal reflection image is (R/2−d). Thereby, the relative position of the optical system to the subject's eye is changed without analyzing the fundus image. Therefore, it is possible to adjust the relative position of the optical system to the subject's eye with high precision so as to suppress the occurrence of flare, without unnecessarily moving the optical system. As a result, the occurrence of flare included in the fundus images can be suppressed with high precision using a simple configuration, while suppressing the degradation of fundus image quality.

In the second aspect of some embodiments, the ophthalmic apparatus in the first aspect further includes an alignment reference position identifying unit (230) configured to identify an alignment reference position on the optical axis relative to the optical system. The controller is configured to control the movement mechanism based on a position (alignment target position) shifted in the optical axis direction by a predetermined amount (shift amount Δs) with reference to the alignment reference position.

According to such an aspect, the occurrence of flare included in the fundus images can be suppressed with high precision using a simple configuration, while suppressing the degradation of fundus image quality.

In the third aspect of some embodiments, the ophthalmic apparatus in the first aspect further includes: an alignment reference position identifying unit (230) configured to identify an alignment reference position on the optical axis relative to the optical system; and a corneal apex position identifying unit (250a) configured to identify a position of a corneal apex of the subject's eye on the optical axis. The controller is configured to control the movement mechanism based on a position (alignment target position) shifted in the optical axis direction by a shift amount ($\Delta s1$) with reference to the alignment reference position, the shift amount being determined based on the position of the corneal apex and the corneal curvature radius of the subject's eye.

According to such an aspect, the corneal apex position of the subject's eye is identified, and the alignment target position is calculated with reference to the alignment reference position. Here, the alignment target position is a position shifted by shift amount in the optical axis direction of the imaging optical system, and the shift amount is determined based on the corneal apex position and the corneal curvature radius. Thereby, the relative position of the optical system to the subject's eye can be adjusted with high precision so as to suppress the occurrence of flare, without unnecessarily moving the optical system.

In the fourth aspect of some embodiments, the ophthalmic apparatus in the first aspect further includes: an alignment reference position identifying unit (230b) configured to identify an alignment reference position on the optical axis relative to the optical system; and a reflection image position identifying unit (corneal reflection image position identifying unit 260b) configured to identify a position of the corneal reflection image on the optical axis. The controller is configured to control the movement mechanism based on a position shifted in the optical axis direction by a shift amount ($\Delta s2$) with reference to the alignment reference position, the shift amount being determined based on the position of the corneal reflection image.

According to such an aspect, the corneal reflection image position of the subject's eye is identified, and the alignment target position is calculated with reference to the alignment reference position. Here, the alignment target position is a position shifted by the shift amount in the optical axis direction of the imaging optical system, and the shift amount is determined based on the identified corneal reflection image position. Thereby, the movement mechanism can be controlled so that the light amount of the returning light passing through the imaging aperture is reduced with higher precision.

In the fifth aspect of some embodiments, the ophthalmic apparatus in any one of the first aspect to the fourth aspect further includes a determination unit (flare determination unit 270c) configured to determine a state of flare based on an image of the fundus obtained by the image sensor. The controller is configured to control the movement mechanism based on a determination result obtained by the determination unit.

According to such an aspect, it is possible to adjust the relative position of the optical system to the subject's eye with high precision so as to suppress the occurrence of flare, while checking the occurrence of flare. As a result, the occurrence of flare included in the fundus images can be suppressed with high precision using a simple configuration, while suppressing the degradation of fundus image quality.

In the sixth aspect of some embodiments, the ophthalmic apparatus in any one of the first aspect to the fourth aspect further includes an operation unit (110). The controller is configured to control the movement mechanism based on an operation content for the operation unit.

According to such an aspect, it is possible to adjust the relative position of the optical system to the subject's eye with high precision so as to suppress the occurrence of flare, while checking the occurrence of flare. As a result, the occurrence of flare included in the fundus images can be suppressed with high precision using a simple configuration, while suppressing the degradation of fundus image quality.

The seventh aspect of some embodiments is an ophthalmic apparatus (1, la. 1d) including: an illumination optical system (20) configured to illuminate a fundus (Ef) of a subject's eye (E) with illumination light; an imaging optical system (40) having an imaging aperture (49) and configured to guide returning light from the subject's eye having passed through the imaging aperture to an imaging sensor (51), an imaging aperture movement mechanism (49D) configured to move the imaging aperture in an optical axis direction of the imaging optical system; and a controller (100, 101a, 101d) configured to control the imaging aperture movement mechanism to change a distance in the optical axis direction of the imaging optical system between an imaging aperture conjugate position substantially conjugate optically to the imaging aperture and a position of a corneal reflection image of the illumination light.

According to such an aspect, a distance in the optical axis direction of the imaging optical system between the imaging aperture conjugate position and the position of the corneal reflection image is changed so that the light amount of the returning light passing through the imaging aperture is less than when the distance in the optical axis direction of the imaging optical system between the imaging aperture conjugate position and the position of the corneal reflection image is (R/2−d). Thereby, the relative position of the optical system to the subject's eye can be adjusted with high precision so as to suppress the occurrence of flare, without unnecessarily moving the optical system. As a result, the occurrence of flare included in the fundus images can be suppressed with high precision using a simple configuration, while suppressing the degradation of fundus image quality.

In the eighth aspect of some embodiments, in the ophthalmic apparatus in the seventh aspect, when a corneal curvature radius is R and a distance from a corneal apex position to the imaging aperture conjugate position is d, the controller is configured to control the imaging aperture movement mechanism so that light amount of the returning light passing through the imaging aperture becomes less than when a distance in the optical axis direction between the imaging aperture conjugate position and a position of the corneal reflection image of the illumination light is (R/2−d).

According to such an aspect, since the imaging aperture is configured to be moved, the occurrence of flare included in the fundus images can be suppressed with high precision using a simple configuration, while suppressing the degradation of fundus image quality.

In the ninth aspect of some embodiments, the ophthalmic apparatus in the seventh aspect of the eighth aspect further includes a corneal apex position identifying unit (250a) configured to identify a position of a corneal apex of the subject's eye on the optical axis. The controller is configured to control the imaging aperture movement mechanism based on a position shifted in the optical axis direction by a shift amount ($\Delta s1$) determined based on the position of the corneal apex and a corneal curvature radius of the subject's eye.

According to such an aspect, the corneal apex position of the subject's eye is identified and the imaging aperture is configured to be moved using the identified corneal apex position. Thereby, the occurrence of flare included in the fundus images can be suppressed with high precision using a simple configuration, while suppressing the degradation of fundus image quality.

In the tenth aspect of some embodiments, the ophthalmic apparatus in the seventh aspect or the eighth aspect further includes a reflection image position identifying unit (corneal reflection image position identifying unit 260*b*) configured to identify the position of the corneal reflection image on the optical axis. The controller is configured to control the imaging aperture movement mechanism based on a position shifted in the optical axis direction by a shift amount determined based on the position of the corneal reflection image.

According to such an aspect, the corneal reflection image position is identified and the imaging aperture is configured to be moved using the identified corneal reflection image position. Thereby, the occurrence of flare included in the fundus images can be suppressed with high precision using a simple configuration, while suppressing the degradation of fundus image quality.

In the eleventh aspect of some embodiments, the ophthalmic apparatus in the seventh aspect or the eighth aspect further includes a determination unit (flare determination unit 270*c*) configured to determine a state of flare based on an image of the fundus obtained by the image sensor. The controller is configured to control the imaging aperture movement mechanism based on a determination result obtained by the determination unit.

According to such an aspect, the imaging aperture can be moved with high precision so as to suppress the occurrence of flare, while checking the occurrence of flare. As a result, the occurrence of flare included in the fundus images can be suppressed with high precision using a simple configuration, while suppressing the degradation of fundus image quality.

In the twelfth aspect of some embodiments, the ophthalmic apparatus in the seventh aspect or the eighth aspect further includes an operation unit (110). The controller is configured to control the imaging aperture movement mechanism based on an operation content for the operation unit.

According to such an aspect, the imaging aperture can be adjusted with high precision so as to suppress the occurrence of flare, while checking the occurrence of flare. As a result, the occurrence of flare included in the fundus images can be suppressed with high precision using a simple configuration, while suppressing the degradation of fundus image quality.

In the thirteenth aspect of some embodiments, the ophthalmic apparatus in the seventh aspect or the eighth aspect further includes a movement mechanism (150) configured to relatively move an optical system and the subject's eye, the optical system including the illumination optical system and the imaging optical system. The controller is configured to control the movement mechanism.

According to such an aspect, the imaging aperture is moved separately from the alignment operation in which the movement mechanism relatively moves the subject's eye and the optical system. Thereby, the relative position of the optical system to the subject's eye can be adjusted with high precision so as to suppress the occurrence of flare, without unnecessarily moving the optical system.

The fourteenth aspect of some embodiments is a method of controlling an ophthalmic apparatus (1, 1*a*, 1*d*) including: an optical system including an illumination optical system (20) and an imaging optical system (40), the illumination optical system being configured to illuminate a fundus (Ef) of a subject's eye (E) with illumination light, the imaging optical system having an imaging aperture (49) and being configured to guide returning light from the subject's eye having passed through the imaging aperture to an imaging sensor (51); a movement mechanism (150) configured to relatively move the subject's eye and the optical system in an optical axis direction of the imaging optical system; and a controller (100, 100*a*, 100*d*, main controller 101, 101*a*, 101*d*) configured to control the movement mechanism. The method of controlling the ophthalmic apparatus includes a control step of controlling the movement mechanism so that light amount of the returning light passing through the imaging aperture becomes less than when a distance in the optical axis direction between an imaging aperture conjugate position substantially conjugate optically to the imaging aperture and a position of a corneal reflection image of the illumination light is (R/2−d), when a corneal curvature radius is R and a distance from a corneal apex position to the imaging aperture conjugate position is d.

According to such an aspect, the relative position of the optical system to the subject's eye is changed so that the light amount of the returning light passing through the imaging aperture is less than when the distance in the optical axis direction of the imaging optical system between the imaging aperture conjugate position and the position of the corneal reflection image is (R/2−d). Thereby, the relative position of the optical system to the subject's eye is changed without analyzing the fundus image. Therefore, it is possible to adjust the relative position of the optical system to the subject's eye with high precision so as to suppress the occurrence of flare, without unnecessarily moving the optical system. As a result, the occurrence of flare included in the fundus images can be suppressed with high precision using a simple configuration, while suppressing the degradation of fundus image quality.

In the fifteenth aspect of some embodiments, the method in the fourteenth aspect further includes an alignment reference position identifying step of identifying an alignment reference position on the optical axis relative to the optical system. The control step is performed to control the movement mechanism based on a position shifted in the optical axis direction by a predetermined amount with reference to the alignment reference position.

According to such an aspect, the occurrence of flare included in the fundus images can be suppressed with high precision using a simple configuration, while suppressing the degradation of fundus image quality.

In the sixteenth aspect of some embodiments, the method in the fourteenth aspect further includes: an alignment reference position identifying step of identifying an alignment reference position on the optical axis relative to the optical system; and a corneal apex position identifying step of identifying a position of the corneal apex of the subject's eye on the optical axis. The control step is performed to control the movement mechanism based on a position shifted in the optical axis direction by a shift amount determined based on the position of the corneal apex and the corneal curvature radius of the subject's eye with reference to the alignment reference position.

According to such an aspect, the corneal apex position of the subject's eye is identified, and the alignment target position is calculated with reference to the alignment reference position. Here, the alignment target position is a position shifted by shift amount in the optical axis direction of the imaging optical system, and the shift amount is determined based on the corneal apex position and the corneal curvature radius. Thereby, the relative position of the optical system to the subject's eye can be adjusted with high precision so as to suppress the occurrence of flare, without unnecessarily moving the optical system.

In the seventeenth aspect of some embodiments, the method in the fourteenth aspect further includes: an alignment reference position identifying step of identifying an alignment reference position on the optical axis relative to the optical system, and a reflection image position identifying step of identifying a position of the corneal reflection image on the optical axis. The control step is performed to control the movement mechanism based on a position shifted in the optical axis direction by a shift amount determined based on the position of the corneal reflection image with reference to the alignment reference position.

According to such an aspect, the corneal reflection image position of the subject's eye is identified, and the alignment target position is calculated with reference to the alignment reference position. Here, the alignment target position is a position shifted by the shift amount in the optical axis direction of the imaging optical system, and the shift amount is determined based on the identified corneal reflection image position. Thereby, the movement mechanism can be controlled so that the light amount of the returning light passing through the imaging aperture is reduced with higher precision.

In the eighteenth aspect of some embodiments, the method in any one of the fourteenth aspect to the seventeenth aspect further includes a determination step of determining a state of flare based on an image of the fundus obtained by the image sensor. The control step is performed to control the movement mechanism based on a determination result obtained in the determination step.

According to such an aspect, it is possible to adjust the relative position of the optical system to the subject's eye with high precision so as to suppress the occurrence of flare, while checking the occurrence of flare. As a result, the occurrence of flare included in the fundus images can be suppressed with high precision using a simple configuration, while suppressing the degradation of fundus image quality.

The nineteenth aspect of some embodiments is a method of controlling an ophthalmic apparatus (1, 1a, 1d) including: an illumination optical system (20) configured to illuminate a fundus (Ef) of a subject's eye (E) with illumination light; an imaging optical system (40) having an imaging aperture (49) and configured to guide returning light from the subject's eye having passed through the imaging aperture to an imaging sensor (51); an imaging aperture movement mechanism (49D) configured to move the imaging aperture in an optical axis direction of the imaging optical system; and a controller (100, 101a, 101d) configured to control the imaging aperture movement mechanism to change a distance in the optical axis direction of the imaging optical system between a position substantially conjugate optically to the imaging aperture and a position of a corneal reflection image of the illumination light. The method of controlling the ophthalmic apparatus includes a control step of controlling the imaging aperture movement mechanism so that light amount of the returning light passing through the imaging aperture becomes less than when a distance in the optical axis direction between an imaging aperture conjugate position substantially conjugate optically to the imaging aperture and a position of a corneal reflection image of the illumination light is (R/2−d), when a corneal curvature radius is R and a distance from a corneal apex position to the imaging aperture conjugate position is d.

According to such an aspect, a distance in the optical axis direction of the imaging optical system between the imaging aperture conjugate position and the position of the corneal reflection image is changed so that the light amount of the returning light passing through the imaging aperture is less than when the distance in the optical axis direction of the imaging optical system between the imaging aperture conjugate position and the position of the corneal reflection image is (R/2−d). Thereby, the relative position of the optical system to the subject's eye can be adjusted with high precision so as to suppress the occurrence of flare, without unnecessarily moving the optical system. As a result, the occurrence of flare included in the fundus images can be suppressed with high precision using a simple configuration, while suppressing the degradation of fundus image quality.

In the twentieth aspect of some embodiments, the method in the nineteenth aspect further includes a corneal apex position identifying step of identifying a position of the corneal apex of the subject's eye on the optical axis. The control step is performed to control the imaging aperture movement mechanism based on a position shifted in the optical axis direction by a shift amount determined based on the position of the corneal apex and a corneal curvature radius of the subject's eye.

According to such an aspect, the corneal apex position of the subject's eye is identified and the imaging aperture is configured to be moved using the identified corneal apex position. Thereby, the occurrence of flare included in the fundus images can be suppressed with high precision using a simple configuration, while suppressing the degradation of fundus image quality.

In the twenty-first aspect of some embodiments, the method in the nineteenth aspect further includes a reflection image position identifying step of identifying a position of the corneal reflection image on the optical axis. The control step is performed to control the imaging aperture movement mechanism based on a position shifted in the optical axis direction by a shift amount determined based on the position of the corneal reflection image.

According to such an aspect, the corneal reflection image position is identified and the imaging aperture is configured to be moved using the identified corneal reflection image position. Thereby, the occurrence of flare included in the fundus images can be suppressed with high precision using a simple configuration, while suppressing the degradation of fundus image quality.

In the twenty-second aspect of some embodiments, the method in the nineteenth aspect further includes a determination step of determining a state of flare based on an image of the fundus obtained by the image sensor. The control step is performed to control the imaging aperture movement mechanism based on a determination result obtained in the determination step.

According to such an aspect, the imaging aperture can be moved with high precision so as to suppress the occurrence of flare, while checking the occurrence of flare. As a result, the occurrence of flare included in the fundus images can be suppressed with high precision using a simple configuration, while suppressing the degradation of fundus image quality.

The twenty-third aspect of some embodiments is a program of causing a computer to execute each step of the method of controlling the ophthalmic apparatus of any one of the fourteenth aspect to the seventeenth aspect, the nineteenth aspect to the twenty-second aspect.

According to such an aspect, the relative position of the optical system to the subject's eye can be adjusted with high precision so as to suppress the occurrence of flare, without unnecessarily moving the optical system. As a result, the occurrence of flare included in the fundus images can be suppressed with high precision using a simple configuration, while suppressing the degradation of fundus image quality.

The embodiments or the modification example thereof described above are merely examples for carrying out the present invention. Those who intend to implement the present invention can apply any modification, omission, addition, or the like within the scope of the gist of the present invention.

In the above embodiments, the ophthalmic apparatus may have arbitrary functions adaptable in the field of ophthalmology. Examples of such functions include an axial length measurement function, a tonometry function, an optical coherence tomography (OCT) function, an ultrasonic inspection, and the like. It should be noted that the axial length measurement function is realized by the OCT, etc. Further, the axial length measurement function may be used to measure the axial length of the subject's eye by projecting light onto the subject's eye and detecting the returning light from the fundus while adjusting the position of the optical system in the Z direction (front-back direction) relative to the subject's eye. The intraocular pressure measurement function is realized by the tonometer, etc. The OCT function is realized by the OCT apparatus, etc. The ultrasonic inspection function is realized by the ultrasonic diagnosis apparatus, etc. Further, the present invention can also be applied to an apparatus (multifunctional apparatus) having two or more of such functions.

In some embodiments, a program for causing a computer to execute the method of controlling the ophthalmic apparatus described above is provided. Such a program can be stored in any non-transitory computer-readable recording medium. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A. B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms: furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus, comprising:
   an optical system including an illumination optical system and an imaging optical system, the illumination optical system being configured to illuminate a fundus of a subject's eye with illumination light, the imaging optical system having an imaging aperture and being configured to guide returning light from the subject's eye having passed through the imaging aperture to an imaging sensor;
   a movement mechanism including an actuator and configured to relatively move the subject's eye and the optical system in an optical axis direction of the imaging optical system; and
   a controller circuit configured to control the movement mechanism, wherein
   when a corneal curvature radius is R and a distance from a corneal apex position to an imaging aperture conjugate position substantially conjugate optically to the imaging aperture is d, the controller is configured to control the movement mechanism so that light amount of the returning light passing through the imaging aperture becomes less than when a distance in the optical axis direction between the imaging aperture conjugate position and a position of a corneal reflection image of the illumination light is (R/2−d).

2. The ophthalmic apparatus of claim 1, further comprising
   processing circuitry configured as an alignment reference position identifying unit configured to identify an alignment reference position on the optical axis relative to the optical system, wherein
   the controller circuit is configured to control the movement mechanism based on a position shifted in the optical axis direction by a predetermined amount with reference to the alignment reference position.

3. The ophthalmic apparatus of claim 1, further comprising:
   processing circuitry configured as an alignment reference position identifying unit configured to identify an alignment reference position on the optical axis relative to the optical system; and
   the processing circuitry further configured as a corneal apex position identifying unit configured to identify a position of a corneal apex of the subject's eye on the optical axis, wherein
   the controller circuit is configured to control the movement mechanism based on a position shifted in the optical axis direction by a shift amount with reference to the alignment reference position, the shift amount being determined based on the position of the corneal apex and the corneal curvature radius of the subject's eye.

4. The ophthalmic apparatus of claim 1, further comprising:
   processing circuitry configured as an alignment reference position identifying unit configured to identify an alignment reference position on the optical axis relative to the optical system; and
   the processing circuitry further configured as a reflection image position identifying unit configured to identify a position of the corneal reflection image on the optical axis, wherein
   the controller circuit is configured to control the movement mechanism based on a position shifted in the optical axis direction by a shift amount with reference to the alignment reference position, the shift amount being determined based on the position of the corneal reflection image.

5. The ophthalmic apparatus of claim 1, further comprising processing circuitry configured as a determination unit configured to determine a state of flare based on an image of the fundus obtained by the image sensor, wherein the controller circuit is configured to control the movement mechanism based on a determination result obtained by the determination unit.

6. The ophthalmic apparatus of claim 1, further comprising an operation unit including a user interface device, wherein the controller circuit is configured to control the movement mechanism based on an operation content for the operation unit.

7. An ophthalmic apparatus, comprising:

an illumination optical system configured to illuminate a fundus of a subject's eye with illumination light;

an imaging optical system having an imaging aperture and configured to guide returning light from the subject's eye having passed through the imaging aperture to an imaging sensor;

an imaging aperture movement mechanism including an imaging aperture actuator and configured to move the imaging aperture in an optical axis direction of the imaging optical system; and a controller circuit configured to control the imaging aperture movement mechanism to change a distance in the optical axis direction of the imaging optical system between an imaging aperture conjugate position substantially conjugate optically to the imaging aperture and a position of a corneal reflection image of the illumination light.

8. The ophthalmic apparatus of claim 7, wherein when a corneal curvature radius is R and a distance from a corneal apex position to the imaging aperture conjugate position is d, the controller circuit is configured to control the imaging aperture movement mechanism so that light amount of the returning light passing through the imaging aperture becomes less than when a distance in the optical axis direction between the imaging aperture conjugate position and a position of the corneal reflection image of the illumination light is $(R/2-d)$.

9. The ophthalmic apparatus of claim 7, further comprising processing circuitry configured as a corneal apex position identifying unit configured to identify a position of a corneal apex of the subject's eye on the optical axis, wherein the controller circuit is configured to control the imaging aperture movement mechanism based on a position shifted in the optical axis direction by a shift amount determined based on the position of the corneal apex and a corneal curvature radius of the subject's eye.

10. The ophthalmic apparatus of claim 7, further comprising processing circuitry configured as a reflection image position identifying unit configured to identify the position of the corneal reflection image on the optical axis, wherein the controller circuit is configured to control the imaging aperture movement mechanism based on a position shifted in the optical axis direction by a shift amount determined based on the position of the corneal reflection image.

11. The ophthalmic apparatus of claim 7, further comprising processing circuitry configured as a determination unit configured to determine a state of flare based on an image of the fundus obtained by the image sensor, wherein the controller circuit is configured to control the imaging aperture movement mechanism based on a determination result obtained by the determination unit.

12. The ophthalmic apparatus of claim 7, further comprising an operation unit including a user interface device, wherein the controller circuit is configured to control the imaging aperture movement mechanism based on an operation content for the operation unit.

13. The ophthalmic apparatus of claim 7, further comprising a movement mechanism including an actuator and configured to relatively move an optical system and the subject's eye, the optical system including the illumination optical system and the imaging optical system, wherein the controller circuit is configured to control the movement mechanism.

14. A method of controlling an ophthalmic apparatus including:

an optical system including an illumination optical system and an imaging optical system, the illumination optical system being configured to illuminate a fundus of a subject's eye with illumination light, the imaging optical system having an imaging aperture and being configured to guide returning light from the subject's eye having passed through the imaging aperture to an imaging sensor;

a movement mechanism including an actuator and configured to relatively move the subject's eye and the optical system in an optical axis direction of the imaging optical system; and a controller circuit configured to control the movement mechanism, the method comprising a control step of controlling the movement mechanism so that light amount of the returning light passing through the imaging aperture becomes less than when a distance in the optical axis direction between an imaging aperture conjugate position substantially conjugate optically to the imaging aperture and a position of a corneal reflection image of the illumination light is $(R/2-d)$, when a corneal curvature radius is R and a distance from a corneal apex position to the imaging aperture conjugate position is d.

15. The method of controlling the ophthalmic apparatus of claim 14, further comprising an alignment reference position identifying step of identifying an alignment reference position on the optical axis relative to the optical system, wherein the control step is performed to control the movement mechanism based on a position shifted in the optical axis direction by a predetermined amount with reference to the alignment reference position.

16. The method of controlling the ophthalmic apparatus of claim 14, further comprising:

an alignment reference position identifying step of identifying an alignment reference position on the optical axis relative to the optical system; and a corneal apex position identifying step of identifying a position of the corneal apex of the subject's eye on the optical axis, wherein the control step is performed to control the movement mechanism based on a position shifted in the optical axis direction by a shift amount determined based on the position of the corneal apex and the corneal curvature radius of the subject's eye with reference to the alignment reference position.

17. The method of controlling the ophthalmic apparatus of claim 14, further comprising:
an alignment reference position identifying step of identifying an alignment reference position on the optical axis relative to the optical system; and
a reflection image position identifying step of identifying a position of the corneal reflection image on the optical axis, wherein
the control step is performed to control the movement mechanism based on a position shifted in the optical axis direction by a shift amount determined based on the position of the corneal reflection image with reference to the alignment reference position.

18. The method of controlling the ophthalmic apparatus of claim 14, further comprising
a determination step of determining a state of flare based on an image of the fundus obtained by the image sensor, wherein
the control step is performed to control the movement mechanism based on a determination result obtained in the determination step.

19. A method of controlling an ophthalmic apparatus including:
an illumination optical system configured to illuminate a fundus of a subject's eye with illumination light;
an imaging optical system having an imaging aperture and configured to guide returning light from the subject's eye having passed through the imaging aperture to an imaging sensor;
an imaging aperture movement mechanism including an actuator and configured to move the imaging aperture in an optical axis direction of the imaging optical system; and
a controller circuit configured to control the imaging aperture movement mechanism to change a distance in the optical axis direction of the imaging optical system between a position substantially conjugate optically to the imaging aperture and a position of a corneal reflection image of the illumination light,
the method comprising
a control step of controlling the imaging aperture movement mechanism so that light amount of the returning light passing through the imaging aperture becomes less than when a distance in the optical axis direction between an imaging aperture conjugate position substantially conjugate optically to the imaging aperture and a position of a corneal reflection image of the illumination light is (R/2−d), when a corneal curvature radius is R and a distance from a corneal apex position to the imaging aperture conjugate position is d.

20. The method of controlling the ophthalmic apparatus of claim 19, further comprising
a corneal apex position identifying step of identifying a position of the corneal apex of the subject's eye on the optical axis, wherein
the control step is performed to control the imaging aperture movement mechanism based on a position shifted in the optical axis direction by a shift amount determined based on the position of the corneal apex and a corneal curvature radius of the subject's eye.

21. The method of controlling the ophthalmic apparatus of claim 19, further comprising
a reflection image position identifying step of identifying a position of the corneal reflection image on the optical axis, wherein
the control step is performed to control the imaging aperture movement mechanism based on a position shifted in the optical axis direction by a shift amount determined based on the position of the corneal reflection image.

22. The method of controlling the ophthalmic apparatus of claim 19, further comprising
a determination step of determining a state of flare based on an image of the fundus obtained by the image sensor, wherein
the control step is performed to control the imaging aperture movement mechanism based on a determination result obtained in the determination step.

23. A computer readable non-transitory recording medium in which a program for causing a computer to execute each step of the method of controlling the ophthalmic apparatus of claim 14 is recorded.

24. A computer readable non-transitory recording medium in which a program for causing a computer to execute each step of the method of controlling the ophthalmic apparatus of claim 19 is recorded.

* * * * *